(12) United States Patent
Wood et al.

(10) Patent No.: US 6,919,343 B2
(45) Date of Patent: Jul. 19, 2005

(54) N-BIPHENYL(SUBSTITUTED METHYL) AMINOCYCLOALKANE-CARBOXAMIDE DERIVATIVES

(75) Inventors: Michael R. Wood, Harleysville, PA (US); Neville J. Anthony, Hatfield, PA (US); Mark G. Bock, Hatfield, PA (US); Dong-Mei Feng, Blue Bell, PA (US); Scott D. Kuduk, Harleysville, PA (US); Dai-Shi Su, Dresher, PA (US); Jenny Miu-chun Wai, Harleysville, PA (US)

(73) Assignee: Merck & Co., Inc., Rahway, NJ (US)

( * ) Notice: Subject to any disclaimer, the term of this patent is extended or adjusted under 35 U.S.C. 154(b) by 224 days.

(21) Appl. No.: 10/354,674

(22) Filed: Jan. 30, 2003

(65) Prior Publication Data

US 2003/0220375 A1 Nov. 27, 2003

Related U.S. Application Data

(60) Provisional application No. 60/410,172, filed on Sep. 12, 2002, and provisional application No. 60/355,062, filed on Feb. 8, 2002.

(51) Int. Cl.⁷ ................... C07C 237/24; C07D 213/82; A61K 31/165
(52) U.S. Cl. .................. 514/256; 514/335; 514/364; 514/378; 514/381; 514/542; 514/616; 544/333; 544/335; 546/316; 548/131; 548/247; 548/250; 560/42; 564/155
(58) Field of Search .................. 544/333, 335; 546/316; 548/131, 250, 247; 560/42; 564/155; 514/256, 335, 364, 378, 381, 542, 616

(56) References Cited

U.S. PATENT DOCUMENTS

| | | | |
|---|---|---|---|
| 5,208,236 A | 5/1993 | Neustadt | |
| 5,270,317 A | 12/1993 | Bernhart et al. | |
| 6,015,812 A | 1/2000 | Ferrari et al. | |
| 6,100,278 A | 8/2000 | Ferrari et al. | |
| 6,313,120 B1 | 11/2001 | Ferrari et al. | |
| 6,433,185 B1 | 8/2002 | Ferrari et al. | |
| 2002/0115685 A1 | 8/2002 | Ferrari et al. | |
| 2003/0073641 A1 | 4/2003 | Ferrari et al. | |

FOREIGN PATENT DOCUMENTS

| | | |
|---|---|---|
| CA | 2050769 | 3/1992 |
| EP | 0 475 898 A1 | 9/1991 |
| EP | 0 655 461 A1 | 5/1995 |
| WO | WO 97/11717 | 4/1997 |
| WO | WO 97/25315 | 7/1997 |
| WO | WO 99/55723 | 11/1999 |
| WO | WO 99/55726 | 11/1999 |
| WO | WO 02/02513 A1 | 1/2002 |
| WO | WO 02/08177 A2 | 1/2002 |
| WO | WO 2003/065789 | 8/2003 |

OTHER PUBLICATIONS

U.S. Appl. No. 10/503,502, filed Aug. 3, 2004, Merck & Co., Inc.

Tetrahedron Letters, vol. 27, No. 19, pp 2143–2144, (1986) by Tateaki Wakamiya, et al.

J. Org. Chem., vol. 59, No. 22, pp 6853–6855, (1984), by Yehiel Gaoni.

*Primary Examiner*—Deepak Rao
(74) *Attorney, Agent, or Firm*—Mollie M. Yang; David L. Rose

(57) ABSTRACT

N-Biphenyl(substituted methyl) aminocycloalkanecarboxamide derivatives are bradykinin B1 antagonists or inverse agonists useful in the treatment or prevention of symptoms such as pain and inflammation associated with the bradykinin B1 pathway.

40 Claims, No Drawings

N-BIPHENYL(SUBSTITUTED METHYL) AMINOCYCLOALKANE-CARBOXAMIDE DERIVATIVES

CROSS REFERENCE TO RELATED APPLICATIONS

This application is based on, and claims priority from, provisional application No. 60/355,062, filed Feb. 8, 2002, and provisional application No. 60/410,172, filed Sep. 12, 2002, each of which is hereby incorporated by reference in its entirety.

BACKGROUND OF THE INVENTION

This invention is directed to aminocycloalkanecarboxamide compounds. In particular, this invention is directed to aminocycloalkanecarboxamide compounds that are bradykinin antagonists or inverse agonists.

Bradykinin ("BK") is a kinin which plays an important role in the pathophysiological processes accompanying acute and chronic pain and inflammation. Bradykinin (BK), like other kinins, is an autacoid peptide produced by the catalytic action of kallikrein enzymes on plasma and tissue precursors termed kininogens. The biological actions of BK are mediated by at least two major G-protein-coupled BK receptors termed B1 and B2. It is generally believed that B2 receptors, but not B1 receptors, are expressed in normal tissues and that inflammation, tissue damage or bacterial infection can rapidly induce B1 receptor expression. This makes the B1 receptor a particularly attractive drug target. The putative role of kinins, and specifically BK, in the management of pain and inflammation has provided the impetus for developing potent and selective BK antagonists. In recent years, this effort has been heightened with the expectation that useful therapeutic agents with analgesic and anti-inflammatory properties would provide relief from maladies mediated through a BK receptor pathway (see e.g., M. G. Bock and J. Longmore, Current Opinion in Chem. Biol., 4:401–406(2000)). Accordingly, there is a need for novel compounds that are effective in blocking or reversing activation of bradykinin receptors. Such compounds would be useful in the management of pain and inflammation, as well as in the treatment or prevention of diseases and disorders mediated by bradykinin; further, such compounds are also useful as research tools (in vivo and in vitro).

Canadian Published Application No. 2,050,769 discloses compounds of the formula:

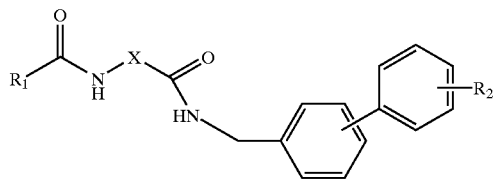

which are intermediates in the preparation of angiotensin II antagonists.

SUMMARY OF THE INVENTION

The present invention provides biphenyl cycloalkanecarboxamide derivatives which are bradykinin antagonists or inverse agonists, pharmaceutical compositions containing such compounds, and methods of using them as therapeutic agents.

DETAILED DESCRIPTION OF THE INVENTION

The present invention provides compounds of formula I and pharmaceutically acceptable salts thereof:

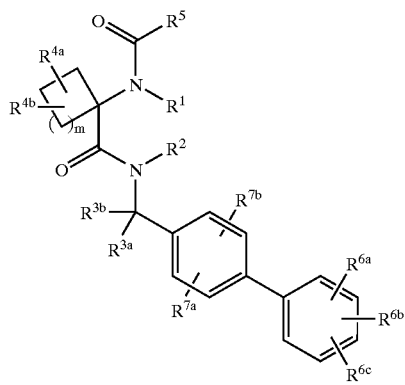

wherein
$R^1$ and $R^2$ are independently selected from
  (1) hydrogen and
  (2) $C_{1-4}$ alkyl;
$R^{3a}$ is selected from
  (1) hydrogen and
  (2) $C_{1-4}$ alkyl optionally substituted with 1 to 5 halogen atoms;
$R^{3b}$ is $C_{1-4}$ alkyl optionally substituted with 1 to 5 halogen atoms;
$R^{4a}$ and $R^{4b}$ are independently selected form
  (1) hydrogen,
  (2) halogen, and
  (3) $C_{1-4}$ alkyl optionally substituted with 1 to 4 groups selected from halogen, $OR^a$, $OC(O)R^a$, $S(O)_kR^d$, $OS(O)_2R^d$, and $NR^1R^2$, or
$R^{4a}$ and $R^{4b}$ together with the carbon atom to which they are both attached form an exo-cyclic methylene optionally substituted with 1 to 2 groups selected from $C_{1-4}$ alkyl optionally substituted with 1–5 halogens and $C_{1-4}$ alkyloxy;
$R^5$ is selected from
  (1) $C_{1-6}$ alkyl optionally substituted with 1 to 5 groups independently selected from halogen, nitro, cyano, $OR^a$, $SR^a$, $COR^a$, $SO_2R^d$, $CO_2R^a$, $OC(O)R^a$, $NR^bR^c$, $NR^bC(O)R^a$, $NR^bC(O)_2R^a$, $C(O)NR^bR^c$, $C_{3-8}$ cycloalkyl,
  (2) $C_{3-8}$ cycloalkyl optionally substituted with 1 to 5 groups independently selected from halogen, nitro, cyano and phenyl,
  (3) $C_{3-6}$ alkynyl,
  (4) $C_{2-6}$ alkenyl optionally substituted with hydroxyethyl,
  (5) $(CH_2)_k$-aryl optionally substituted with 1 to 3 groups independently selected from halogen, nitro, cyano, $OR^a$, $SR^a$, $C(O)_2R^a$, $C_{1-4}$ alkyl and $C_{1-3}$ haloalkyl, wherein aryl is selected from phenyl, 3,4-methylenedioxyphenyl and naphthyl;
  (6) $(CH_2)_k$-heterocycle optionally substituted with 1 to 3 groups independently selected from halogen, nitro, cyano, $OR^a$, $SR^a$, $C_{1-4}$ alkyl and $C_{1-3}$ haloalkyl wherein said heterocycle is selected from (a) a 5-membered heteroaromatic ring having a ring heteroatom selected from N, O and S, and optionally having up to 3 additional ring nitrogen atoms wherein said ring is optionally benzo-fused; (b) a 6-membered heteroaromatic ring containing from 1 to 3 ring nitrogen atoms and N-oxides thereof, wherein said ring is optionally benzo-fused; and (c) a 5- or 6-membered non-aromatic heterocyclic ring selected from tetrahydrofuranyl, 5-oxo-tetrahydrofuranyl, 2-oxo-2H-pyranyl, 6-oxo-1,6-dihydropyridazinyl, (7) $C(O)_2R^a$, and
(8) $C(O)NR^bR^c$;

$R^{6a}$ is selected from
(1) $C_{1-8}$ alkyl optionally substituted with 1–5 groups independently selected from halogen, nitro, cyano, $COR^a$, $CO_2R^a$, $C(O)NR^bR^c$, $OR^a$, $OC(O)R^a$, $SR^a$, $SO_2R^d$, $S(O)R^d$, $NR^bR^c$, $NR^bC(O)R^a$, $NR^bSO_2R^d$, $NR^bCO_2R^a$,
(2) $C_{3-8}$ cycloalkyl,
(3) $C_{2-8}$ alkenyl optionally substituted with $CO_2R^a$,
(4) halogen,
(5) cyano,
(6) nitro,
(7) $NR^bR^c$,
(8) $NR^bC(O)R^a$,
(9) $NR^bCO_2R^a$,
(10) $NR^bC(O)NR^bR^c$,
(11) $NR^bC(O)NR^bCO_2R^a$,
(12) $NR^bSO_2R^d$,
(13) $CO_2R^a$,
(14) $COR^a$,
(15) $C(O)NR^bR^c$,
(16) $C(O)NHOR^a$,
(17) $C(=NOR^a)R^a$,
(18) $C(=NOR^a)NR^bR^c$,
(19) $OR^a$,
(20) $OC(O)R^a$,
(21) $S(O)_kR^d$,
(22) $SO_2NR^bR^c$, and
(23) optionally substituted heterocycle where the heterocycle is a 5-membered heteroaromatic ring having a ring heteroatom selected from N, O and S, and optionally having up to 3 additional ring nitrogen atoms, 4,5-dihydro-oxazolyl and 4,5-dihydro-1,2,4-oxadiazolyl, and wherein said substituent is 1 to 3 groups independently selected from $C_{1-4}$ alkyl optionally substituted with 1 to 5 halogen atoms, $OR^a$ or $OC(O)R^a$, $R^{6b}$ and $R^{6c}$ are independently selected from
(1) hydrogen, and
(2) a group from $R^{6a}$; with the proviso that not more than one of
$R^{6a}$, $R^{6b}$, and $R^{6c}$ is a heterocycle;

$R^{7a}$ and $R^{7b}$ are independently selected from
(1) hydrogen,
(2) halogen,
(3) cyano,
(4) nitro,
(5) $OR^a$,
(6) $CO_2R^a$,
(7) $C(O)NR^bR^c$,
(8) $C_{1-4}$ alkyl optionally substituted with 1 to 5 halogen atoms,
(9) $NR^bR^c$, and
(10) $S(O)_kR^d$;

$R^a$ is selected from
(1) hydrogen,
(2) $C_{1-4}$ alkyl optionally substituted with 1 to 5 halogen atoms,
(3) phenyl optionally substituted with 1 to 3 groups independently selected from halogen, cyano, nitro, OH, $C_{1-4}$ alkyloxy, $C_{3-6}$ cycloalkyl and $C_{1-4}$ alkyl optionally substituted with 1 to 5 halogen atoms,
(4) $C_{3-6}$ cycloalkyl, and
(5) pyridyl optionally substituted with 1 to 3 groups independently selected from halogen and $C_{1-4}$ alkyl;

$R^b$ and $R^c$ are independently selected from
(1) hydrogen,
(2) $C_{1-4}$ alkyl optionally substituted with 1 to 5 groups independently selected from halogen, amino, mono-$C_{1-4}$alkylamino, di-$C_{1-4}$alkylamino, and $SO_2R^d$,
(3) $(CH_2)_k$-phenyl optionally substituted with 1 to 3 groups selected from halogen, cyano, nitro, OH, $C_{1-4}$ alkyloxy, $C_{3-6}$ cycloalkyl and $C_{1-4}$ alkyl optionally substituted with 1 to 5 halogen atoms, and
(4) $C_{3-6}$ cycloalkyl, or $R^b$ and $R^c$ together with the nitrogen atom to which they are attached form a 4-, 5-, or 6-membered ring optionally containing an additional heteroatom selected from N, O, and S; or $R^b$ and $R^c$ together with the nitrogen atom to which they are attached form a cyclic imide;

$R^d$ is selected from
(1) $C_{1-4}$ alkyl optionally substituted with 1 to 5 halogen atoms,
(2) $C_{1-4}$ alkyloxy, and
(3) phenyl optionally substituted with 1 to 3 groups selected from halogen, cyano, nitro, OH, $C_{1-4}$ alkyloxy, $C_{3-6}$ cycloalkyl and $C_{1-4}$ alkyl optionally substituted with 1 to 5 halogen atoms;

k is 0, 1 or 2; and
m is 0 or 1.

For compounds of formula I, examples of $R^1$ and $R^2$ include hydrogen, methyl, ethyl, n-propyl, isopropyl, n-butyl, t-butyl, isobutyl and sec-butyl. In one embodiment of formula I are compounds wherein $R^1$ and $R^2$ are each hydrogen.

Examples of $R^{3a}$ and $R^{3b}$ for compounds of formula I include hydrogen, methyl, ethyl, n-propyl, isopropyl, n-butyl, t-butyl, isobutyl, sec-butyl, chloromethyl, fluromethyl, trifluoromethyl, 2,2,2-trifluoroethyl, 2,2-difluoroethyl, 1,1,2,2,2-pentafluoroethyl, and the like. In one embodiment of formula I are compounds wherein one of $R^{3a}$ is hydrogen and $R^{3b}$ is $C_{1-4}$ alkyl. In one subset thereof $R^{3b}$ is methyl.

Examples $R^{4a}$ and $R^{4b}$ or compounds of formula I include hydrogen, methyl, ethyl, n-propyl, isopropyl, n-butyl, sec-butyl, isobutyl, t-butyl, chlorine, fluorine, bromine, chloromethyl, 1-chloroethyl, hydroxymethyl, 2-methoxyethyl, ethoxymethyl, acetyloxymethyl, methylthiomethyl, aminomethyl, methylamino-methyl, (dimethylamino)methyl, (methylsulfonyl)oxymethyl, and the like; or $R^{4a}$ and $R^{4b}$ on the same carbon atom taken together represent methylene. In one embodiment of formula I are compounds wherein one of $R^{4a}$ and $R^{4b}$ is hydrogen and the other is selected from hydrogen, halogen and $C_{1-4}$ alkyl optionally substituted with a group selected from halogen, $OR^a$, $OC(O)R^a$, $S(O)_kR^d$, $OS(O)_2R^d$, and $NR^1R^2$, or $R^{4a}$ and $R^{4b}$ together with the carbon atom to which they are both attached form an exo-cyclic methylene. In one subset thereof $R^{4a}$ and $R^{4b}$ are each hydrogen; in another subset $R^{4a}$ is hydrogen and $R^{4b}$ is selected from $CH_2$-halogen, $CH_2$—$OR^a$, $CH_2$—$OC(O)R^a$, $CH_2$—$S(O)_k$ $R^d$, $CH_2$—$OS(O)_2R^d$, and $CH_2$—$NR^1R^2$; in a further subset $R^{4a}$ is hydrogen and $R^{4b}$ is selected from hydroxymethyl, acetyloxymethyl, chloromethyl, (methanesulfonyl) oxymethyl, (methylthio)methyl and (dimethylamino) methyl.

Examples of $R^5$ for compounds of formula I include methyl, ethyl, n-propyl, isopropyl, n-butyl, sec-butyl, isobutyl, t-butyl, 1-ethylpropyl, 2,2-dimethylpropyl, bromomethyl, chloromethyl, dichloromethyl, difluoromethyl, trifluoromethyl, chlorodifluoromethyl, cyanomethyl, aminomethyl, acetylaminomethyl, dimethylaminomethyl, hydroxymethyl, methoxymethyl, ethoxymethyl, methylsulfonylmethyl, phenylthiomethyl, phenoxymethyl, 1-aminoethyl, 1-acetylaminomethyl, 1-imidazolylmethyl, t-butoxycarbonylaminomethyl, 3-pyridylcarbonylmethyl, 1-chloroethyl, 1,1-dichloroethyl, 2,2,2-trifluoroethyl, pentafluoroethyl, 2-methoxyethyl, 2-phenylethyl, 2-cyclopentylethyl, 2-carboxyethyl, 2-methoxy-2-oxoethyl, 2-nitroethyl, 1,1-difluoro-1-hydroxypropyl, 1-hydroxypropyl, 2-oxopropyl, 3-methoxy-3-oxopropyl, 1-cyano-cyclopropyl, cyclopropyl, cyclopentyl, 2-phenylcyclopropyl, allyl, ethenyl, 1-(1-hydroxyethyl)vinyl, 3-butynyl, propargyl, phenyl, benzyl, 3,5-bis(trifluoromethyl)phenyl, 2,4-difluorophenyl, 4-methylphenyl, 3,4-dimethoxybenzyl, 3,4-dimethoxyphenyl, 4-cyanophenyl, 3-nitrophenyl, 2-naphthyl, 3,4-methylenedioxyphenyl, 3-cyanophenyl, 2-cyanophenyl, 3-fluorophenyl, 3-methoxyphenyl, 3-chlorophenyl, 3,4-dichlorophenyl, 3,5-dimethoxyphenyl, 3-trifluoromethylphenyl, 3-methylphenyl, 3,5-dichlorophenyl, 2-hydroxyphenyl, 3-hydroxyphenyl, 3-nitro-5-(trifluoromethyl)phenyl, 5-isoxazolyl, 2-benzothienyl, 2-thienylmethyl, 3-pyridyl, 4-pyridyl, 2-furyl, 3-furyl, 2-thienyl, 3-thienyl, 5-methyl-3-isoxazolyl, 3-tetrahydrofuranyl, 4-methyl-1,2,5-oxadiazol-3-yl, 5-carboxy-3-pyridyl, 6-hydroxy-2-pyridyl, 5-hydroxy-3-pyridyl, 2-hydroxy-3-pyridyl, 2-methyoxy-3-pyridyl, 6-chloro-2-pyridyl, 2-chloro-3-pyridyl, 5-chloro-3-pyridyl, 5-fluoro-3-pyridyl, 5-bromo-3-pyridyl, 5-methyl-3-pyridyl, 3-(trifluoromethyl)-4-pyridyl, 5-(trifluoromethyl)-3-pyridyil, 1-methyl-4-pyrazolyl, 1-pyrazolylmethyl, 1-methyl-2-imidazolyl, 1,2,4-triazol-1-ylmethyl, 4-thiazolyl, 5-oxo-tetrahydrofuran-2-yl, 2-oxo-5-pyranyl, 3-isoxazolyl, 3-pyridazinyl, 5-pyrimidinyl, 4-pyrimidinyl, 1-methyl-5-pyrazolyl, 1-methyl-3-pyrazolyl, 5-thiazolyl, 5-methyl-1-pyrazolylmethyl, (3-methyl-1,2,4-triazol-5-yl) methyl, 2-(1,2,4-triazol-1-yl)ethyl, 5-methyl-4-thiazolyl, 2-quinoxalinyl, methoxycarbonyl, aminocarbonyl, methylaminocarbonyl, dimethylaminocarbonyl, 2-(dimethylamino)ethylaminocarbonyl, benzylaminocarbonyl, 2-phenethylaminocarbonyl.

In one embodiment of formula I are compounds wherein $R^5$ is $C_{1-6}$ alkyl optionally substituted with 1 to 5 groups independently selected from halogen, nitro, cyano, $OR^a$, $SR^a$, $COR^a$, $SO_2R^d$, $CO_2R^a$, $OC(O)R^a$, $NR^bR^c$, $NR^bC(O)$ $R^a$, $NR^bCO_2R^a$, $C(O)NR^bR^c$, and $C_{3-8}$ cycloalkyl. In one subset thereof are compounds wherein $R^5$ is $C_{1-5}$ alkyl optionally substituted with 1 to 5 groups independently selected from halogen, nitro, cyano, $OR^a$, $SR^a$, $CO_2R^a$ and $C_{3-8}$ cycloalkyl. In a further subset are compounds wherein $R^5$ is selected from $C_{1-5}$ alkyl and $C_{1-3}$ alkyl substituted with 1 to 5 groups selected from halogen, cyano, hydroxy, $C_{1-4}$ alkoxy and $C_{1-4}$ alkoxycarbonyl. In another further subset $R^5$ is selected from $C_{1-3}$ alkyl substituted with 1 to 5 halogen atoms, or a group selected from cyano, hydroxy, $C_{1-4}$ alkoxy and $C_{1-4}$ alkoxycarbonyl.

In another embodiment of formula I are compounds wherein $R^5$ is $C_{3-6}$ cycloalkyl optionally substituted with 1 to 3 groups independently selected from halogen, nitro, cyano and phenyl. In one subset $R^5$ is $C_{3-6}$ cycloalkyl optionally substituted with a group selected from cyano and phenyl.

In another embodiment of formula I are compounds wherein $R^5$ is $(CH_2)_k$-aryl optionally substituted with 1 to 3 groups independently selected from halogen, nitro, cyano, $OR^a$, $SR^a$, $C_{1-4}$ alkyl and $C_{1-3}$ haloalkyl, wherein aryl is selected from phenyl, 3,4-methylenedioxyphenyl and naphthyl. In one subset thereof, $R^5$ is phenyl optionally substituted with 1 to 3 groups independently selected from halogen, trifluoromethyl, nitro, cyano, $C_{1-4}$ alkoxy and $C_{1-4}$ alkyl; in a further subset $R^5$ is phenyl optionally substituted with 1 to 2 groups selected from methyl, trifluoromethyl, halogen, cyano, nitro and methoxy.

In another embodiment of formula I are compounds wherein $R^5$ is $(CH_2)_k$-heterocycle optionally substituted with 1 to 2 groups independently selected from halogen, nitro, cyano, $OR^a$, $SR^a$, $C_{1-4}$ alkyl and $C_{1-3}$ haloalkyl wherein said heterocycle is selected from isoxazolyl, thienyl, pyridinyl, benzothienyl, furyl, tetrahydrofuranyl, oxadiazolyl, 1-oxidopyridinyl, pyrazolyl, imidazolyl, 1,2,4-triazolyl, thiazolyl, 5-oxotetrahydrofuranyl, 2-oxo-2H-pyranyl, 6-oxo-1,6-dihydropyridazinyl, oxazolyl, pyridazinyl, pyrimidinyl and quinoxalinyl. In one subset thereof $R^5$ is selected from isoxazolyl optionally substituted with 1 or 2 $C_{1-4}$ alkyl, thienyl, pyridinyl optionally substituted with hydroxy, trifluoromethyl or halogen, benzothienyl, furyl, tetrahydrofuranyl, oxadiazolyl optionally substituted with $C_{1-4}$ alkyl, 1-oxidopyridinyl optionally substituted with halogen or $C_{1-4}$ alkyl, pyrazolyl optionally substituted with $C_{1-4}$ alkyl, imidazolyl optionally substituted with $C_{1-4}$ alkyl, 1,2,4-triazolyl optionally substituted with $C_{1-4}$ alkyl, thiazolyl optionally substituted with $C_{1-4}$ alkyl, 5-oxotetrahydrofuranyl, 2-oxo-2H-pyranyl, 6-oxo-1,6-dihydropyridazinyl, oxazolyl, pyridazinyl, pyrimidinyl and quinoxalinyl. In another subset $R^5$ is selected from 5-isoxazolyl, 5-pyrimidinyl, 5-bromo-3-pyridyl and N-oxide thereof, and 5-trifluoromethyl-3-pyridyl.

For compounds of formula I examples of $R^{6a}$ include 1-methylethyl, 1-hydroxyethyl, methoxymethyl, 2-oxo-2-methoxyethyl, carboxy, methoxycarbonyl, ethoxycarbonyl, isopropoxycarbonyl, phenoxycarbonyl, cyclopentoxycarbonyl, cyclobutoxycarbonyl, cyclopropoxycarbonyl, 2,2,2-trifluoroethoxycarbonyl, 4-trifluoromethylphenoxycarbonyl, methoxyaminocarbonyl, methoxycarbonylmethyl, formyl, hydroxy, 3-methyl-1,2,4-oxadiazol-5-yl, 5-methyl-1,2,4-oxadiazol-3-yl, 1-methyl-5-tetrazolyl, 2-methyl-5-tetrazolyl, cyano, hydroxy, methoxy, difluoromethoxy, trifluoromethoxy, trifluoromethyl, chloro, fluoro, methylaminosulfonyl, dimethylaminosulfonyl, methoxycarbonylamino, ethoxycarbonylamino, 2-fluoroethoxycarbonylamino, isopropoxycarbonylamino, methylaminocarbonylamino, dimethylamino, methylaminocarbonyl, isopropylaminocarbonyl, ethylaminocarbonyl, cyclopropylaminocarbonyl, cyclobutylaminocarbonyl, dimethylaminocarbonyl and aminocarbonyl; examples for $R^{6b}$ for compounds of formula I include hydrogen, chloro, fluoro, methyl and methoxycarbonyl; example of $R^{6c}$ include hydrogen, chloro, fluoro and methyl; and examples of $R^{7a}$ and $R^{7b}$ include hydrogen, hydroxy, methoxy, methylamino, methylsulfonyl, chloro and fluoro.

In another embodiment of formula I are compounds wherein m is 0.

In another embodiment of formula I are compounds represented by formula I(1):

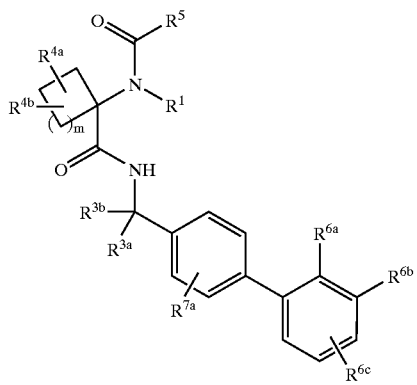

I(1)

wherein m, $R^1$, $R^2$, $R^{3a}$, $R^{3b}$, $R^{4a}$, $R^{4b}$, $R^5$, $R^{6a}$, $R^{6b}$, $R^{6c}$ and $R^{7a}$ have the same definitions as provided under formula I.

In a subset of formula I(1) are compounds wherein $R^{6a}$ is selected from (1) $CO_2R^a$, (2) $C(O)NHOR^a$, (3) cyano, (4) halogen, (5) $OR^a$, (6) $C_{1-8}$ alkyl optionally substituted with 1–5 halogen atoms, or a group selected from $CO_2R^a$, $C(O)NR^bR^c$ and $OR^a$, (7) $C(O)NR^bR^c$, (8) $NR^bC(O)NR^bR^c$, (9) $NR^bC(O)R^a$, and (10) optionally substituted heterocycle where the heterocycle is selected from oxadiazolyl and tetrazolyl and wherein said substituent is 1 to 3 groups independently selected from $C_{1-4}$ alkyl optionally substituted with 1 to 5 halogen atoms, $OR^a$ or $OC(O)R^a$. In a further subset are compounds wherein $R^{6a}$ is selected from $CO_2R^a$, $C(O)NHOR^a$, methyltetrazolyl, methyloxadiazolyl, $NR^bC(O)NR^bR^c$, and $NR^bC(O)OR^a$.

In another subset of formula I(1) are compounds wherein $R^{6b}$ is selected from hydrogen, halogen and $CO_2R^a$. In a further subset $R^{6b}$ is hydrogen or halogen.

In another subset of formula I(1) are compounds where $R^{6a}$ is selected from (1) $CO_2R^a$, (2) $C(O)NHOR^a$, (3) cyano, (4) halogen, (5) $OR^a$, (6) $C_{1-8}$ alkyl optionally substituted with 1–5 halogen atoms, or a group selected from $CO_2R^a$, $C(O)NR^bR^c$ and $OR^a$, (7) $C(O)NR^bR^c$, (8) $NR^bC(O)NR^bR^c$, (9) $NR^bC(O)R^a$, and (10) optionally substituted heterocycle where the heterocycle is selected from oxadiazolyl and tetrazolyl and wherein said substituent is 1 to 3 groups independently selected from $C_{1-4}$ alkyl optionally substituted with 1 to 5 halogen atoms, $OR^a$ or $OC(O)R^a$; $R^{6b}$ is selected from hydrogen and halogen; and $R^{6c}$ is hydrogen.

In another subset of formula I(1) are compounds wherein $R^5$ is selected from $C_{1-4}$ alkyl optionally substituted with 1 to 5 halogen atoms or a cyano group, $C_{3-6}$ cycloalkyl, isoxazolyl, pyrimidinyl and pyridinyl (and N-oxide thereof) optionally substituted with halogen.

In another embodiment of formula I are compounds represented by formula I(2):

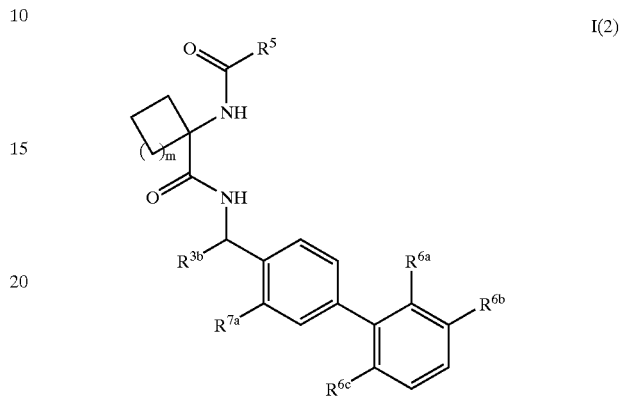

I(2)

wherein m, $R^{3b}$, $R^5$, $R^{6a}$, $R^{6b}$, $R^{6c}$ and $R^{7a}$ have the same definitions as provided under formula I.

In one embodiment of formula I(2), $R^{3b}$ is methyl.

In another embodiment of formula I(2), $R^{6b}$ is hydrogen or halogen. In one subset $R^{6b}$ is hydrogen; in another subset $R^{6b}$ is fluorine or chlorine.

In another embodiment of formula I(2), $R^{6a}$ is selected from (1) $CO_2R^a$, (2) $C(O)NHOR^a$, (3) cyano, (4) halogen, (5) $OR^a$, (6) $C_{1-8}$ alkyl optionally substituted with 1–5 halogen atoms, or a group selected from $CO_2R^a$, $C(O)NR^bR^c$ and $OR^a$, (7) $C(O)NR^bR^c$, (8) $NR^bC(O)NR^bR^c$, (9) $NR^bC(O)OR^a$, and (10) optionally substituted heterocycle where the heterocycle is selected from oxadiazolyl and tetrazolyl and wherein said substituent is 1 to 3 groups independently selected from $C_{1-4}$ alkyl optionally substituted with 1 to 5 halogen atoms, $OR^a$ or $OC(O)R^a$. In one subset $R^{6a}$ is selected from $CO_2R^a$, $C(O)NHOR^a$, methyltetrazolyl, methyloxadiazolyl, $NR^bC(O)NR^bR^c$, and $NR^bC(O)OR^a$. In a further subset $R^{6a}$ is selected from $CO_2R^a$, methyltetrazolyl and methyloxadiazolyl, In another embodiment of formula I(2), $R^{6c}$ is hydgrogen or halogen. In one subset $R^{6c}$ is hydgrogen.

In another embodiment $R^{7a}$ is hydrogen or halogen. In one subset $R^{7a}$ is hydrogen. In another subset $R^{7a}$ is fluorine. In yet another subset $R^{6a}$ is hydrogen, fluorine or chlorine, and $R^{7a}$ is hydrogen or fluorine.

In another embodiment of formula I(2) $R^5$ is selected from $C_{1-4}$ alkyl optionally substituted with 1 to 5 halogen atoms or a cyano group, $C_{3-6}$ cycloalkyl, isoxazolyl, pyrimidinyl and pyridinyl (and N-oxide thereof) optionally substituted with halogen.

In another embodiment of formula I are compounds of formula I(3):

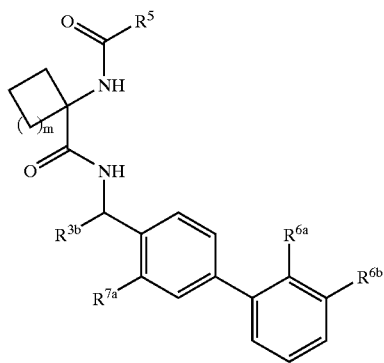

wherein m is 0 or 1, $R^{6a}$ is 2-methyl-2H-tetrazol-5-yl, 3-methyl-1,2,4-oxadiazol-5-yl $CO_2R^a$ or $C(O)NHOR^a$ wherein $R^a$ is $C_{1-4}$ alkyl, particularly methyl; $R^{6b}$ is hydrogen, fluorine or chlorine; $R^{3b}$ is $C_{1-4}$ alkyl, particularly methyl; $R^5$ is selected from $C_{1-4}$ alkyl optionally substituted with 1 to 5 halogen atoms or a cyano group, $C_{3-6}$ cycloalkyl, isoxazolyl, pyrimidinyl and pyridinyl (and N-oxide thereof) optionally substituted with halogen or trifluoromethyl, particularly trifluoromethyl, difluoromethyl, chlorodifluromethyl, 2,2,2-trifluoroethyl, pentafluoromethyl, cyanomethyl, 5-pyrimidinyl, 5-isoxazolyl and 5-bromo-3-pyridinyl and N-oxide thereof; and $R^{7a}$ is hydrogen or fluorine.

Some representative compounds are:

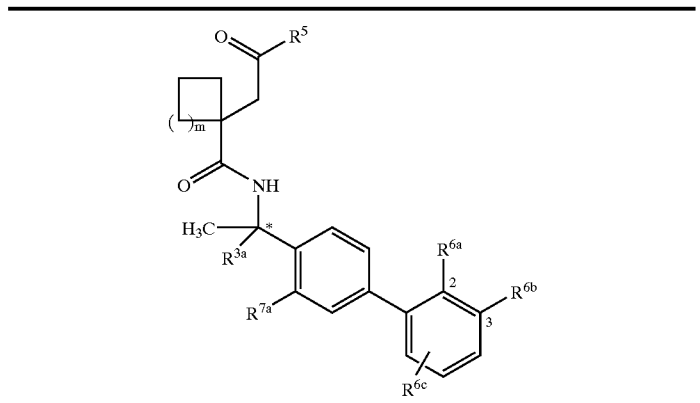

| m | $R^5$ | $R^{6a}$ | $R^{6b}$ | $R^{6c}$ | $R^{7a}$ | * |
|---|---|---|---|---|---|---|
| | | $R^{3a}$ is H unless otherwise specified | | | | |
| 0 | $CH_2CF_3$ | $CO_2CH_3$ | F | H | H | R |
| 0 | $CH_2CF_3$ | $CONHOCH_3$ | F | H | H | R |
| 0 | $CF_3$ | $CO_2CH_3$ | F | H | H | § |
| 0 | $CF_3$ | 3-$CH_3$-1,2,4-oxadiazol-5-yl | F | H | F | R |
| 0 | $CF_3$ | $CO_2CH_3$ | Cl | H | F | R |
| 0 | $CF_3$ | 2-$CH_3$-tetrazol-5-yl | F | H | F | R |
| 0 | $CH_2CN$ | $CO_2CH_3$ | F | H | H | R |
| 0 | $CH_2CN$ | $CO_2CH_3$ | Cl | H | H | R |
| 0 | $CH_2CF_3$ | $CO_2CH_3$ | Cl | H | H | R |
| 0 | $CH_2CF_3$ | $CO_2CH_3$ | F | H | F | (±) |
| 0 | isoxazol-5-yl | $CO_2CH_3$ | F | H | F | (±) |
| 0 | $CH_2CN$ | $CO_2CH_3$ | F | H | F | (±) |
| 0 | pyrimidin-5-yl | $CO_2CH_3$ | F | H | H | R |
| 0 | $CH_2CF_3$ | $CO_2CH_3$ | F | H | F | S |
| 0 | $CH_2CF_3$ | $CO_2CH_3$ | F | H | F | R |
| 0 | pyrimidin-5-yl | $CO_2CH_3$ | F | H | F | (±) |
| 0 | isoxazol-5-yl | $CO_2CH_3$ | F | H | F | R |
| 0 | $CF_3$ | $CO_2CH_3$ | F | H | F | R |
| 0 | pyrimidin-5-yl | $CO_2CH_3$ | F | H | F | R |
| 0 | isoxazol-5-yl | $CO_2CH_3$ | F | H | F | S |
| 0 | $CF_3$ | $CO_2CH_3$ | F | H | F | S |
| 0 | pyrimidin-5-yl | $CO_2CH_3$ | F | H | F | S |
| 0 | $CH_3$ | $CO_2CH_3$ | F | H | F | R |
| 0 | 5-Br-pyridin-3-yl | $CO_2CH_3$ | F | H | F | R |
| 0 | 5-Br-1-oxido-pyridin-3-yl | $CO_2CH_3$ | F | H | F | R |
| 0 | $CF_3$ | $CO_2CH_3$ | H | H | F | R |
| 0 | pyrimidin-5-yl | $CO_2CH_3$ | H | H | F | R |
| 0 | $CClF_2$ | $CO_2CH_3$ | F | H | F | R |
| 0 | 5-($CF_3$)pyridin-3-yl | $CO_2CH_3$ | F | H | F | R |
| 0 | $CClF_2$ | $CO_2CH_3$ | Cl | H | F | R |
| 0 | $CHF_2$ | $CO_2CH_3$ | F | H | F | R |

-continued

| | | | | | | |
|---|---|---|---|---|---|---|
| 0 | CF₂CF₃ | CO₂CH₃ | F | H | F | R |
| 0 | CHF₂ | CO₂CH₃ | Cl | H | F | R |
| 0 | CH₃ | 3-CH₃-1,2,4-oxadiazol-5-yl | F | H | H | R |
| 0 | CH₂CN | 3-CH₃-1,2,4-oxadiazol-5-yl | F | H | H | R |
| 0 | CH₂CF₃ | 3-CH₃-1,2,4-oxadiazol-5-yl | F | H | H | R |
| 0 | isoxazol-5-yl | 3-CH₃-1,2,4-oxadiazol-5-yl | F | H | H | R |
| 0 | CH₂CF₃ | 3-CH₃-1,2,4-oxadiazol-5-yl | F | H | F | S |
| 0 | CH₂CF₃ | 3-CH₃-1,2,4-oxadiazol-5-yl | F | H | F | R |
| 0 | CH₂CN | 3-CH₃-1,2,4-oxadiazol-5-yl | F | H | F | (±) |
| 0 | CH₂CF₃ | 3-CH₃-1,2,4-oxadiazol-5-yl | F | H | F | (±) |
| 0 | pyrimidin-5-yl | 3-CH₃-1,2,4-oxadiazol-5-yl | F | H | F | (±) |
| 0 | CClF₂ | 3-CH₃-1,2,4-oxadiazol-5-yl | F | H | F | R |
| 0 | pyrimidin-5-yl | 3-CH₃-1,2,4-oxadiazol-5-yl | F | H | F | R |
| 0 | CHF₂ | 3-CH₃-1,2,4-oxadiazol-5-yl | F | H | F | R |
| 0 | CH₂CN | 2-CH₃-tetrazol-5-yl | F | H | H | R |
| 0 | CH₂CF₃ | 2-CH₃-tetrazol-5-yl | F | H | H | R |
| 0 | CH₂CN | 1-CH₃-tetrazol-5-yl | F | H | H | R |
| 0 | CH₂CF₃ | 1-CH₃-tetrazol-5-yl | F | H | H | R |
| 0 | CH₃ | 1-CH₃-tetrazol-5-yl | F | H | H | R |
| 0 | isoxazol-5-yl | 2-CH₃-tetrazol-5-yl | F | H | F | (±) |
| 0 | CH₂CF₃ | 2-CH₃-tetrazol-5-yl | F | H | F | (±) |
| 0 | pyrimidin-5-yl | 2-CH₃-tetrazol-5-yl | F | H | F | (±) |
| 0 | CF₃ | 2-CH₃-tetrazol-5-yl | F | H | F | S |
| 0 | CClF₂ | 2-CH₃-tetrazol-5-yl | F | H | F | R |
| 0 | CHF₂ | 2-CH₃-tetrazol-5-yl | F | H | F | R |
| 0 | CH₂CF₃ | cyano | F | H | H | R |
| 0 | CH₂CF₃ | difluoromethoxy | H | H | H | R |
| 0 | CH₂CF₃ | trifluoromethoxy | H | H | H | R |
| 0 | CH₂CF₃ | trifluoromethyl | F | H | H | R |
| 0 | CH₂CF₃ | Cl | Cl | H | H | R |
| 0 | isoxazol-5-yl | trifluoromethyl | F | H | H | R |
| 0 | CH₂CN | trifluoromethyl | F | H | H | R |
| 0 | isoxazol-5-yl | Cl | Cl | H | H | R |
| 0 | CH₂CN | Cl | Cl | H | H | R |
| 0 | CH₂CN | F | CO₂Me | H | H | R |
| 0 | cyclopropyl | cyano | F | H | H | R |
| 0 | CH₂CF₃ | CON(CH₃)₂ | F | H | H | R |
| 0 | pyrimidin-5-yl | NHCO₂CH₃ | F | H | H | R |
| 0 | pyrimidin-5-yl | NHCONHCH₃ | F | H | H | R |
| 0 | CF₃ | CONHCH₃ | F | H | H | R |
| 0 | CF₃ | CONHCH₃ | Cl | H | H | R |
| 0 | CH₂CF₃ | CONHCH₃ | F | H | H | R |
| 0 | isoxazol-5-yl | CONHOCH₃ | F | H | H | R |
| 0 | CH₂CF₃ | CONH-cyclopropyl | F | H | H | R |
| 0 | CH₂CF₃ | CONH-cyclobutyl | F | H | H | R |
| 0 | CH₂CF₃ | 5-CH₃-1,2,4-oxadiazol-3-yl | F | H | H | R |
| 0 | isoxazol-5-yl | 5-CH₃-1,2,4-oxadiazol-3-yl | F | H | H | R |
| 0 | pyrimidin-5-yl | 5-CH₃-1,2,4-oxadiazol-3-yl | H | H | F | R |
| 0 | CF₃ | 5-CH₃-1,2,4-oxadiazol-3-yl | H | H | F | R |
| 0 | pyrimidin-5-yl | 5-CH₃-1,2,4-oxadiazol-3-yl | H | 5-Cl | F | R |
| 0 | CF₃ | 5-CH₃-1,2,4-oxadiazol-3-yl | H | 5-Cl | F | R |
| 0 | pyrimidin-5-yl | 5-CH₃-1,2,4-oxadiazol-3-yl | H | 5-CH₃ | F | R |
| 0 | CF₃ | 5-CH₃-1,2,4-oxadiazol-3-yl | H | 5-CH₃ | F | R |
| 0 | pyrimidin-5-yl | 5-CH₃-1,2,4-oxadiazol-3-yl | H | 5-F | F | R |
| 0 | CF₃ | 5-CH₃-1,2,4-oxadiazol-3-yl | H | 5-F | F | R |
| 0 | pynmidin-5-yl | methoxy | F | 5-F | H | R |
| 0 | CF₃ | methoxy | F | 5-F | H | R |
| 0 | pyrimidin-5-yl | 2-CH₃-2H-tetrazol-5-yl | H | 5-F | F | R |
| 0 | CF₃ | 2-CH₃-2H-tetrazol-5-yl | H | 5-F | F | R |
| 0 | CF₃ | CO₂CH₃ | H | 5-Cl | F | R |
| 0 | CClF₂ | CO₂CH₃ | H | 5-Cl | F | R |
| 0 | CF₃ | CO₂CH₃ | H | 5-CH₃ | F | R |
| 0 | CClF₂ | CO₂CH₃ | H | 5-CH₃ | F | R |
| 0 | CF₃ | 3-CH₃-1,2,4-oxadiazol-5-yl | H | 5-F | F | R |
| 0 | CF₃ | 3-CH₃-1,2,4-oxadiazol-5-yl | H | 5-Cl | F | R |
| 0 | CClF₂ | 3-CH₃-1,2,4-oxadiazol-5-yl | H | 5-Cl | F | R |
| 0 | CF₃ | 3-CH₃-1,2,4-oxadiazol-5-yl | H | 5-CH₃ | F | R |
| 0 | CClF₂ | 3-CH₃-1,2,4-oxadiazol-5-yl | H | 5-CH₃ | F | R |
| 0 | CF₃ | CO₂CH₃ | H | 5-F | F | R |
| 0 | CClF₂ | CO₂CH₃ | H | 5-F | F | R |
| 0 | pyrimidin-5-yl | 2-CH₃-2H-tetrazol-5-yl | H | 5-Cl | F | R |
| 0 | CF₃ | 2-CH₃-2H-tetrazol-5-yl | H | 5-Cl | F | R |
| 0 | pyrimidin-5-yl | 2-CH₃-2H-tetrazol-5-yl | H | 5-CH₃ | F | R |
| 0 | CF₃ | 2-CH₃-2H-tetrazol-5-yl | H | 5-CH₃ | F | R |
| 0 | CF₃ | CONHCH₃ | Cl | H | F | R |
| 0 | CF₃ | NHCO₂CH₃ | Cl | H | F | R |
| 0 | CF₃ | NHCO₂CH(CH₃)₂ | Cl | H | F | R |
| 0 | pyrimidin-5-yl | NHCO₂CH(CH₃)₂ | Cl | H | F | R |
| 0 | CF₃ | NHCO₂CH₃ | F | H | F | R |

-continued

| | | | | | | |
|---|---|---|---|---|---|---|
| 0 | CF$_3$ | 2-methoxy-2-oxoethyl | F | H | F | R |
| 0 | CF$_3$ | CONHCH$_3$ | F | H | F | R |
| 0 | CF$_3$ | CH$_2$OCH$_3$ | Cl | H | F | R |
| 0 | CF$_3$ | hydroxy | Cl | 5-Cl | H | R |
| 0 | pyrimidin-5-yl | NHCO$_2$CH$_3$ | F | H | F | R |
| 0 | pyrimidin-5-yl | NHCO$_2$CH$_3$ | Cl | H | F | R |
| 0 | CF$_3$ | CO$_2$CH$_3$ | H | 6-CH$_3$ | F | R |
| 0 | CClF$_2$ | CO$_2$CH$_3$ | H | 6-CH$_3$ | F | R |
| 0 | CF$_3$ | CO$_2$CH$_3$ | Cl | H | F | R |
| 0 | CF$_3$ | CO$_2$CH$_3$ | CH$_3$ | H | F | R |
| 0 | CClF$_2$ | CO$_2$CH$_3$ | CH$_3$ | H | F | R |
| 1 | pyrimidin-5-yl | CO$_2$CH$_3$ | F | H | H | § |
| 1 | CF$_3$ | 3-CH$_3$-1,2,4-oxadiazol-5-yl | F | H | F | R |
| 1 | CClF$_2$ | 3-CH$_3$-1,2,4-oxadiazol-5-yl | F | H | F | R |
| 1 | pyrimidin-5-yl | 3-CH$_3$-1,2,4-oxadiazol-5-yl | F | H | F | R |
| 1 | CF$_3$ | CO$_2$CH$_3$ | F | H | F | R |
| 1 | CClF$_2$ | CO$_2$CH$_3$ | F | H | F | R |
| 1 | pyrimidin-5-yl | CO$_2$CH$_3$ | F | H | F | R |
| 1 | pyrimidin-5-yl | CO$_2$CH$_3$ | F | H | H | R |
| 1 | pyrimidin-5-yl | 2-CH$_3$-2H-tetrazol-5-yl | F | H | F | R |
| 1 | CF$_3$ | CO$_2$CH$_3$ | Cl | H | F | R |
| 1 | CClF$_2$ | CO$_2$CH$_3$ | Cl | H | F | R |
| 1 | CHF$_2$ | CO$_2$CH$_3$ | Cl | H | F | R |

*stereoconfiguration at the indicated carbon,
§R$^{3a}$ is CH$_3$

\* stereoconfiguration at the indicated carbon,
§ R$^{3a}$ is CH$_3$

Unless otherwise stated, the following terms have the meanings indicated below:

"Alkyl" as well as other groups having the prefix "alk" such as, for example, alkoxy, alkanoyl, alkenyl, alkynyl and the like, means carbon chains which may be linear or branched or combinations thereof. Examples of alkyl groups include methyl, ethyl, propyl, isopropyl, butyl, sec- and tert-butyl, pentyl, hexyl, heptyl and the like.

"Alkenyl" means a linear or branched carbon chain containing at least one C═C bond. Examples of alkenyl include allyl, 2-butenyl, 3-butenyl, 1-methyl-2-propenyl, and the like.

"Alkynyl" means a linear or branched carbon chain containing at least one C≡C bond. Examples of alkynyl include propargyl, 2-butynyl, 3-butynyl, 1-methyl-2-propynyl, and the like.

"Cyclic imide" includes succinimide, maleimide, phthalirmide and the like.

"Cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include cyclopropyl, cyclobutyl, cyclopentyl, cyclohexyl, decahydronaphthalene, adamantane, indanyl, indenyl, fluorenyl, 1,2,3,4-tetrahydronaphthalene and the like.

"Haloalkyl" means an alkyl radical as defined above wherein at least one and up to all of the hydrogen atoms are replaced with a halogen. Examples of such haloalkyl radicals include chloromethyl, 1-bromoethyl, fluoromethyl, difluoromethyl, trifluoromethyl, 2,2,2-trifluoroethyl and the like.

"Halogen" means fluorine, chlorine, bromine and iodine.

"Optionally substituted" is intended to include both substituted and unsubstituted. Thus, for example, optionally substituted aryl could represent a pentafluorophenyl or a phenyl ring.

Optical Isomers—Diastereomers—Geometric Isomers—Tautomers

Compounds described herein may contain an asymmetric center and may thus exist as enantiomers. Where the compounds according to the invention possess two or more asymmetric centers, they may additionally exist as diastereomers. The present invention includes all such possible stereoisomers as substantially pure resolved enantiomers, racemic mixtures thereof, as well as mixtures of diastereomers. The above Formula I is shown without a definitive stereochemistry at certain positions. The present invention includes all stereoisomers of Formula I and pharmaceutically acceptable salts thereof. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general Formula I may be obtained by stereospecific synthesis using optically pure starting materials or reagents of known configuration.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Salts

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from pharmaceutically acceptable organic non-toxic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, dicyclohexylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

Prodrugs

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

Pharmaceutical Compositions

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compound represented by Formula I, or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Tablet | mg/tablet |
|---|---|
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

Utilities

Compounds of this invention are antagonists or inverse agonists of bradykinin receptor, in particular the bradykinin B1 receptor, and as such are useful in the treatment and prevention of diseases and conditions mediated through the bradykinin receptor pathway such as pain and inflammation. The compounds would be effective in the treatment or prevention of pain including, for example, visceral pain (such as pancreatitis, interstitial cystitis, renal colic), neuropathic pain (such as postherpetic neuralgia, nerve injury, the "dynias", e.g., vulvodynia, phantom limb pain, root avulsions, painful traumatic mononeuropathy, painful polyneuropathy), central pain syndromes (potentially caused by virtually any lesion at any level of the nervous system), and postsurgical pain syndromes (eg, postmastectomy syndrome, postthoracotomy syndrome, stump pain)), bone and joint pain (osteoarthritis), repetitive motion pain, dental pain, cancer pain, myofascial pain (muscular injury, fibromyalgia), perioperative pain (general surgery, gynecological), chronic pain, dysmennorhea, as well as pain associated with angina, and inflammatory pain of varied origins (e.g. osteoarthritis, rheumatoid arthritis, rheumatic disease, teno-synovitis and gout).

Further, the compounds of this invention can also be used to treat hyperreactive airways and to treat inflammatory events associated with airways disease e.g. asthma including allergic asthma (atopic or non-atopic) as well as exercise-induced bronchoconstriction, occupational asthma, viral- or bacterial exacerbation of asthma, other non-allergic asthmas and "wheezy-infant syndrome". Compounds of the present invention may also be used to treat chronic obstructive pulmonary disease including emphysema, adult respiratory distress syndrome, bronchitis, pneumonia, allergic rhinitis (seasonal and perennial), and vasomotor rhinitis. They may also be effective against pneumoconiosis, including aluminosis, anthracosis, asbestosis, chalicosis, ptilosis, siderosis, silicosis, tabacosis and byssinosis.

Compounds of the present invention may also be used for the treatment of inflammatory bowel disease including Crohn's disease and ulcerative colitis, irritable bowel syndrome, pancreatitis, nephritis, cystitis (interstitial cystitis), uveitis, inflammatory skin disorders such as psoriasis and eczema, rheumatoid arthritis and edema resulting from trauma associated with burns, sprains or fracture, cerebral edema and angioedema. They may be used to treat diabetic vasculopathy, diabetic neuropathy, diabetic retinopathy, post capillary resistance or diabetic symptoms associated with insulitis (e.g. hyperglycemia, diuresis, proteinuria and increased nitrite and kallikrein urinary excretion). They may be used as smooth muscle relaxants for the treatment of spasm of the gastrointestinal tract or uterus. Additionally, they may be effective against liver disease, multiple sclerosis, cardiovascular disease, e.g. atherosclerosis, congestive heart failure, myocardial infarct; neurodegenerative diseases, eg. Parkinson's and Alzheimers disease, epilepsy, septic shock e.g. as anti-hypovolemic and/or anti-hypotensive agents, headache including cluster headache, migraine including prophylactic and acute use, closed head trauma, cancer, sepsis, gingivitis, osteoporosis, benign prostatic hyperplasia and hyperactive bladder. Animal models of these diseases and conditions are generally well known in the art, and may be suitable for evaluating compounds of the present invention for their potential utilities. Finally, compounds of the present invention are also useful as research tools (in vivo and in vitro).

The compounds of this invention are useful in the treatment of pain and inflammation by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

The compounds would be effective in the treatment or prevention of pain including, for example, bone and joint pain (osteoarthritis), repetitive motion pain, dental pain, cancer pain, myofascial pain (muscular injury, fibromyalgia), perioperative pain (general surgery, gynecological) and chronic pain by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

In particular, inflammatory pain such as, for example, inflammatory airways disease (chronic obstructive pulmonary disease) would be effectively treated by the compounds of this invention by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

Further, the compounds of this invention can additionally be used to treat asthma, inflammatory bowel disease, rhinitis, pancreatitis, cystitis (interstitial cystitis), uveitis, inflammatory skin disorders, rheumatoid arthritis and edema resulting from trauma associated with burns, sprains or fracture by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

They may be used subsequent to surgical intervention (e.g. as post-operative analgesics) and to treat inflammatory pain of varied origins (e.g. osteoarthritis, rheumatoid arthritis, rheumatic disease, teno-synovitis and gout) as well as for the treatment of pain associated with angina, menstruation or cancer by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

They may be used to treat diabetic vasculopathy, post capillary resistance or diabetic symptoms associated with insulitis (e.g. hyperglycemia, diuresis, proteinuria and increased nitrite and kallikrein urinary excretion) by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

They may be used to treat inflammatory skin disorders such as psoriasis and eczema by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

They may be used as smooth muscle relaxants for the treatment of spasm of the gastrointestinal tract or uterus or in the therapy of Crohn's disease, ulcerative colitis or pancreatitis by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

Such compounds may be used therapeutically to treat hyperreactive airways and to treat inflammatory events associated with airways disease e.g. asthma, and to control, restrict or reverse airways hyperreactivity in asthma by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

They may be used to treat intrinsic and extrinsic asthma including allergic asthma (atopic or non-atopic) as well as exercise-induced broncho-constriction, occupational asthma, viral or bacterial exacerbated asthma, other non-allergic asthmas and "wheezy-infant syndrome" by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

They may also be effective against pneumoconiosis, including aluminosis, anthracosis, asbestosis, chalicosis, ptilosis, siderosis, silicosis, tabacosis and byssinosis was well as adult respiratory distress syndrome, chronic obstructive pulmonary or airways disease, bronchitis, allergic rhinitis, and vasomotor rhinitis by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

Additionally, they may be effective against liver disease, multiple sclerosis, atherosclerosis, Alzheimer's disease, septic shock e.g. as anti-hypovolemic and/or anti-hypotensive agents, cerebral edema, headache including cluster headache, migraine including prophylactic and acute use, closed head trauma, irritable bowel syndrome and nephritis by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to: (1) morphine and other opiate receptor agonists including propoxyphene (Darvon); (2) non-steroidal antiinflammatory drugs (NSAIDs) including COX-2 inhibitors such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone), and the coxibs (celecoxib, valecoxib, rofecoxib and etoricoxib); (3) corticosteroids such as betamethasone, budesonide, cortisone, dexamethasone, hydrocortisone, methylprednisolone, prednisolone, prednisone and triamcinolone; (4) histamine H1 receptor antagonists such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, desloratadine, fexofenadine and levocetirizine; (5) histamine H2 receptor antagonists such as cimetidine, famotidine and ranitidine; (6) proton pump inhibitors such as omeprazole, pantoprazole and esomeprazole; (7) leukotriene antagonists and 5-lipoxygenase inhibitors such as zafirlukast, montelukast, pranlukast and zileuton; (8) drugs used for angina, myocardial ischemia including nitrates such as nitroglycerin and isosorbide nitrates, beta blockers such as atenolol, metoprolol, propranolol, acebutolol, betaxolol, bisoprolol, carteolol, labetalol, nadolol, oxprenolol, penbutolol, pindolol, sotalol and timolol, and calcium channel blockers such as diltiazam, verapamil, nifedipine, bepridil, felodipine, flunarizine, isradipine, nicardipine and nimodipine; (9) incontinence medications such as antimuscarinics, e.g., tolterodine and oxybutinin); (10) gastrointestinal antispasmodics (such as atropine, scopolamine, dicyclomine, antimuscarinics, as well as diphenoxylate); skeletal muscle relaxants (cyclobenzaprine, carisoprodol, chlorphenesin, chlorzoxazone, metaxalone, methocarbamol, baclofen, dantrolene, diazepam, or orphenadrine); (11) gout medications such as allopurinol, probenicid and colchicine; (12) drugs for rheumatoid arthritis such as methotrexate, auranofin, aurothioglucose and gold sodium thiomalate; (13) drugs for osteoporosis such as alendronate and raloxifene; decongestants such as pseudoephedrine and phenylpropanolamine; (14) local anesthetics; (15) anti-herpes drugs such as acyclovir, valacyclovir and famcyclovir; and (15) anti-emetics such as ondansetron and granisetron.

Biological Evaluation

Assessing the Affinity of Selected Compounds to Bind to the Bradykinin B1 or B2 Receptor Radioligand binding assays are performed using membranes from CHO cells that stably express the human, rabbit, rat, or dog B1 receptors or CHO cells that express the human B2 receptor. For all receptor types, cells are harvested from culture flasks in PBS/1 mM EDTA and centrifuged at 1000×g for 10 minutes. The cell pellets are homogenized with a polytron in ice cold 20 mM HEPES, 1 mM EDTA, pH 7.4 (lysis buffer) and centrifuged at 20,000×g for 20 minutes. The membrane pellets are rehomogenized in lysis buffer, centrifuged again at 20,000×g and the final pellets are resuspended at 5 mg protein/ml in assay buffer (120 mM NaCl, 5 mM KCl, 20 mM HEPES, pH 7.4) supplemented with 1% BSA and frozen at −800° C.

On the day of assay, membranes are centrifuged at 14,000×g for 5 minutes and resuspended to the desired protein concentration in assay buffer containing 100 nM enaliprilat, 140 µg/mL bacitracin and 0.1% BSA. 3H-des-arg10, leu9 kallidin is the radioligand used for the human and rabbit B1 receptors, 3H-des-arg10 kallidin is used for the rat and dog B1 receptors, and 3H-bradykinin is used to label the human B2 receptor.

For all assays, compounds are diluted from DMSO stock solutions with 4 µL added to assay tubes for a final DMSO concentration of 2%. This is followed by the addition of 100 µL radioligand and 100 µL of the membrane suspension. Nonspecific binding for the B1 receptor binding assays is determined using 1 µM des-arg10 kallidin and nonspecific binding for the B2 receptor is determined with 1 µM bradykinin. Tubes are incubated at room temperature (22° C.) for 60 minutes followed by filtration using a Tomtec 96-well harvesting system. Radioactivity retained by the filter is counted using a Wallac Beta-plate scintillation counter.

The compounds of this invention have affinity for the B1 receptor in the above assay as demonstrated by results of less than 5 µM. It is advantageous that the assay results be less than 1 µM, even more advantageous for the results be less than 0.5 µM. It is further advantageous that compounds of this invention have affinity for the bradykinin B1 receptor over the bradykinin B2 receptor; more advantageously, the affinity for the B1 receptor is at least 10 fold, and preferably over 100 fold, over that for the B2 receptor.

Assay for Bradykinin B1 Antagonists

B1 agonist-induced calcium mobilization was monitored using a Fluorescence Imaging Plate Reader (FLIPR). CHO cells expressing the B1 receptor were plated in 96 or 384 well plates and allowed to incubate in Iscove's modified DMEM overnight. Wells were washed two times with a physiological buffered salt solution and then incubated with 4 uM Fluo-3 for one hour at 37° C. The plates were then washed two times with buffered salt solution and 100 uL of buffer was added to each well. Plates were placed in the FLIPR unit and allowed to equilibrate for two minutes. The test compound was then added in 50 ul volumes followed five minutes later by 50 ul of agonist (des-arg$^{10}$ kallidin). Relative fluorescence peak heights in the absence and presence of antagonist were used to calculate the degree of inhibition of the B1 receptor agonist response by the test compound. Eight to ten concentrations of test compound were typically evaluated to construct an inhibition curve and determine IC50 values using a four-parameter nonlinear regression curve fitting routine.

Assay for Bradykinin Inverse Agonists

Inverse agonist activity at the human B1 receptor was evaluated using transiently transfected HEK293 cells. One day following transfection cell flasks were labeled overnight with 6 uCi/ml [$^3$H]myo-inositol. On the day of assay, the media was removed and the attached cells were gently rinsed with 2×20 ml of phosphate-buffered saline. Assay buffer (HEPES buffered physiological salts, pH 7.4) was added and the cells were detached by tapping of the flask. The cells were centrifuged at 800×g for five minutes and resuspended at 1×10$^6$ cells/ml in assay buffer supplemented with 10 mM lithium chloride. After 10 minutes at room temperature, one-half ml aliquots were distributed to tubes containing test compound or vehicle. After an additional 10 minutes the tubes were transferred to a 37° C. water bath for 30 minutes. The incubation was terminated by the addition of a 12% perchloric acid solution and the tubes were placed on ice for 30 minutes. The acid was then neutralized with KOH and the tubes centrifuged to pellet precipitated material. [$^3$H]Inositol monophosphate formed was recovered by standard ion exchange chromatographic techniques and quantitated by liquid scintillation counting. Inverse agonist activity was determined by the degree to which a test compound reduced basal (cells incubated with vehicle) levels of [$^3$H]inositol monophosphate accumulation.

Abbreviations Used

The following abbreviations have the meanings indicated, unless stated otherwise in the specification:
BOC (boc) t-butyloxycarbonyl
DCM dichloromethane
DMF dimethylformamide
DMSO Dimethyl sulfoxide
EDC or EDCI 1-(3-dimethylaminopropyl)3-ethylcarbodiimide HCl
eq. equivalent(s)
ES (or ESI)-MS electron spray ionization-mass spectroscopy
Et ethyl
EtOAc ethyl acetate
EtOH ethanol
FAB-MS fast atom bombardment-mass spectroscopy
HOBt 1-hydroxybenzotriazole hydrate
HPLC high pressure liquid chromatography
LCMS Liquid chromatography/mass spectroscopy
LHMDS lithium bis(trimethylsilyl)amide
Me methyl
MeOH Methanol
MHz megahertz
MsCl Mesyl chloride
NEt$_3$ Triethylamine
NMR nuclear magnetic resonance
TFA trifluoroacetic acid
THF tetrahydrofuran Compounds of formula I may be prepared according to the following illustrative schemes.

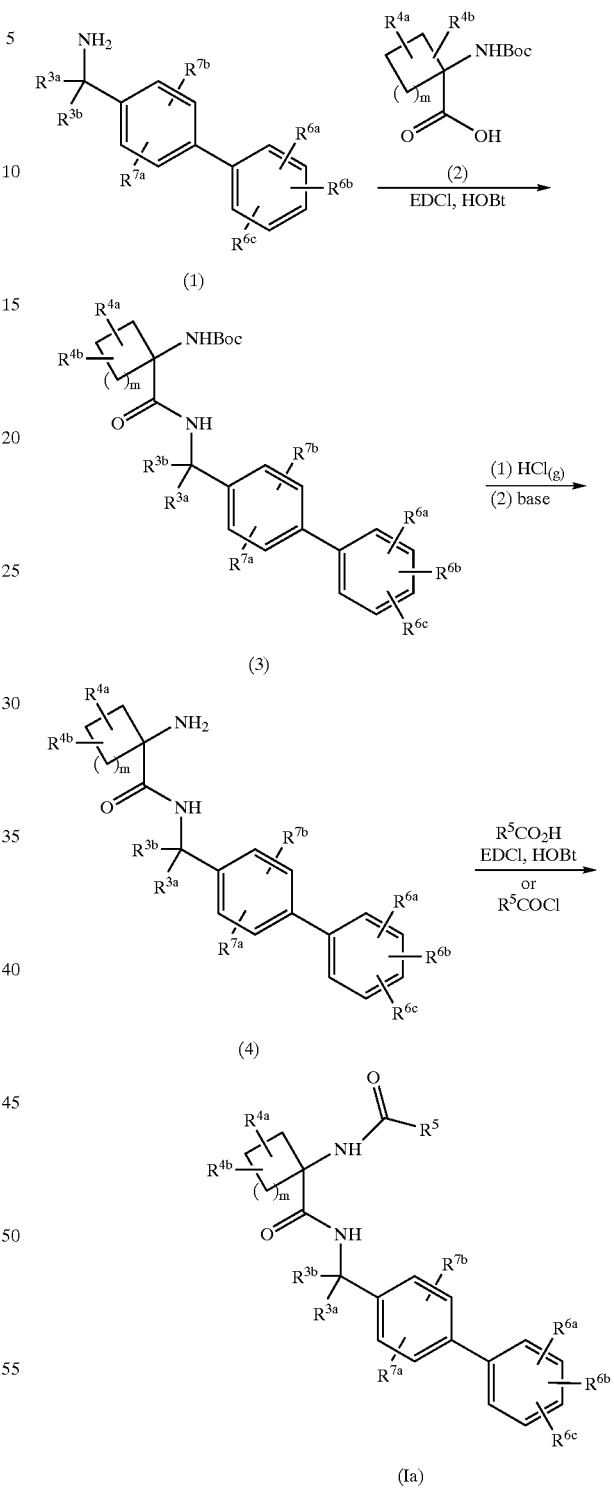

In Scheme 1, compound (Ia) is assembled by coupling the biarylmethanamine derivative (1) to the protected aminocycloalkanoic acid (2) using standard peptide coupling reagent combinations, such as EDCI/HOBt, in an appropriate solvent, such as THF, to provide (3). The Boc protecting group is then removed by the action of an acid, like HCl, in an appropriate solvent, like MeOH, to yield an ammonium salt from which the free-base derivative (4) may be obtained using an appropriate base, such as ammonia, and an appropriate solvent, such as chloroform. This amine derivative (4) is then reacted with a carboxylic acid or carboxylic acid equivalent to yield title compound (Ia). Alternatively, the acid-salt of (4) can be used in the final reaction to yield title compound (Ia) provided an appropriate base such as triethylamine is added.

Alternatively, compound (Ia) may be assembled by coupling the biarylmethanamine derivative (1), with the acylated aminocycloalkanoic acid (5) as shown in Scheme 1a.

SCHEME 1a

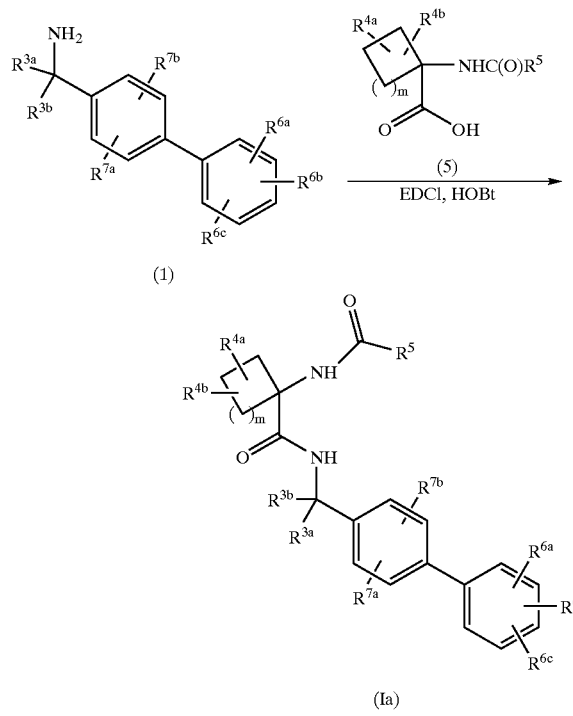

A number of synthetic strategies may be employed to assemble the intermediate biarylmethanamine derivative (1) as shown in Schemes 2a–2c.

SCHEME 2a

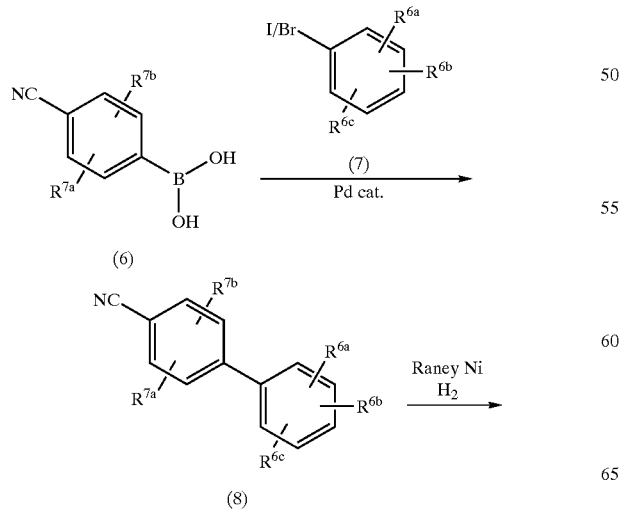

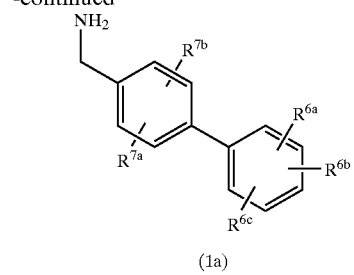

In Scheme 2a, the cyanobiaryl derivative (8) is assembled using a Suzuki reaction between an aromatic boronic acid derivative (6), or an appropriate boronic ester derivative, and an aromatic halide (7) in the presence of a triarylphosphine, like triphenylphosphine, and a metal catalyst, like palladium acetate. The resultant cyano biaryl intermediate (8) is then catalytically reduced to the corresponding amine biaryl derivative (1a) using hydrogen and a metal, such as Raney Ni, in an appropriate solvent.

Alternatively, as illustrated in Scheme 2b, a methanamine derivative (9), after primary amine protection with an appropriate protecting group such as Boc, is elaborated to the pinacol boron ester (11) using a palladium catalyst in an appropriate solvent, like dimethyl sulfoxide. This boron ester (11) is coupled to an aryl halide derivative (7) employing Suzuki reaction conditions to yield (1).

SCHEME 2b

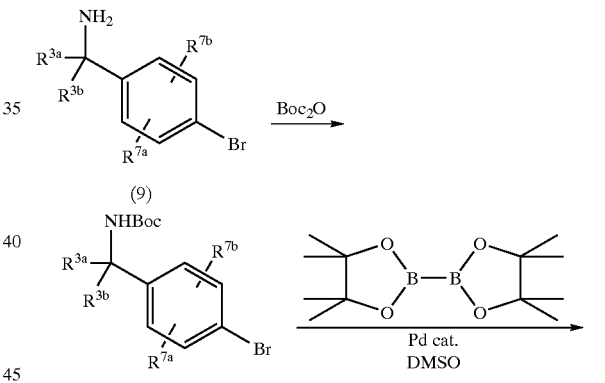

A third method for the preparation of biarylmethanamine derivatives is depicted in Scheme 2c. The biaryl moiety (14) is first assembled using a palladium catalyzed coupling of (12) with an aryl zinc compound (13) as shown. The methyl group of biaryl (14) is then elaborated according to the three step sequence of halogenation, nucleophilic displacement of the halogen with azide, and reduction to provide the corresponding amine intermediate (1a). Alternatively, the biarylmethanamine (1a) can also be prepared starting from the arylcarbonitrile (16) and aryl zinc compuond (13) as previously discussed. The resulting biarylcarbonitrile (8) is then reduced using hydrogen to provide (1a).

strong acid, like TFA, and second by alkaline hydrolysis in a suitable mixture of water and an organic solvent, like methanol, at a temperature between 25 and 100° C. to yield the amino acid derivative (17). Prior activation of a carboxylic acid ($R^5COOH$) with an appropriate set of peptide coupling reagents, like EDCI/HOBt, forms the 'active ester' which then reacts with the amino acid derivative (17) to yield (18). The latter compound can either react with amines ($HNR^bR^c$) or alkyloxy amines ($H_2NOR^a$) under the action of an appropriate set of peptide coupling reagents, like EDCI/HOBt, to form the claimed compounds (Ib) and (Ic), respectively.

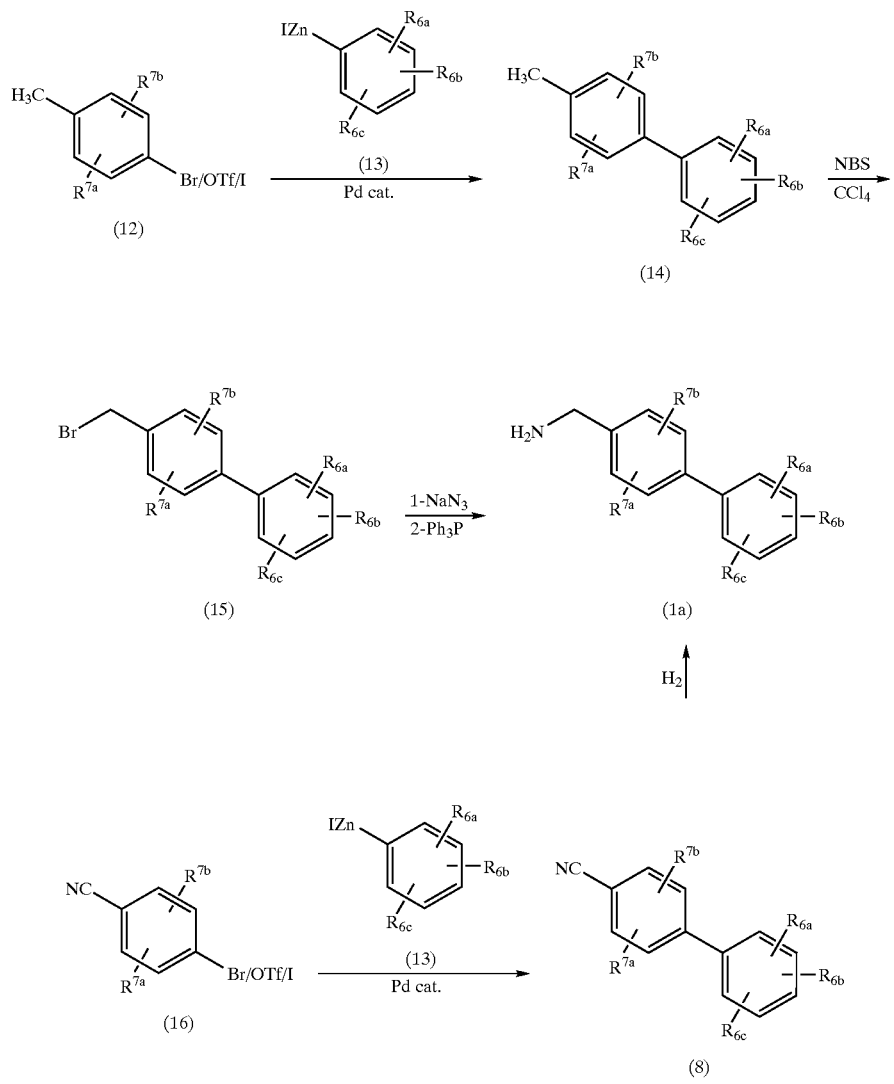

SCHEME 2c

It will be appreciated by persons skilled in the art that functional group interconversion can be used to provide various compounds of formula I. As illustrated in Scheme 3, derivative (3a) is bis-deprotected first by the action of a

SCHEME 3

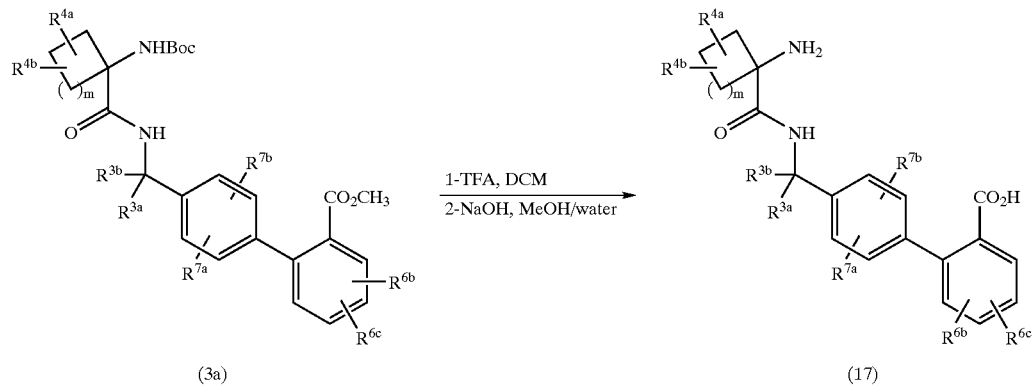

(3a) → (17)

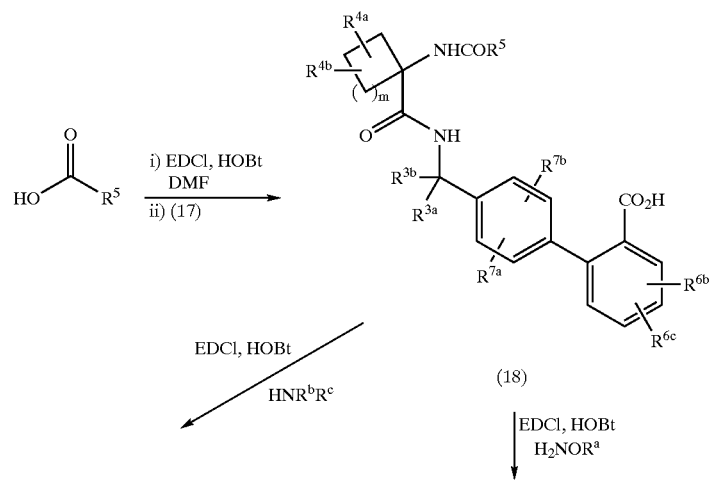

(18)

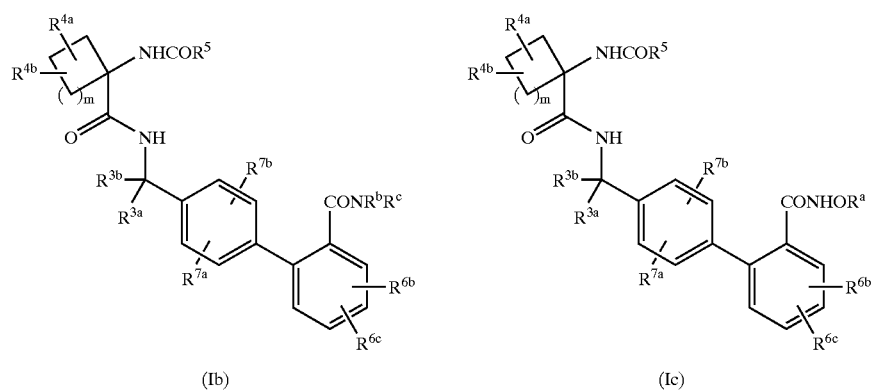

(Ib)   (Ic)

N-alkylation is illustrated in Scheme 4. The amine (4) is alkylated with excess alkyl iodide (I—$R^1$) in an appropriate solvent, like THF, in the presence of an acid scavenger, like triethylamine, at elevated temperatures to provide (19), along with bis-alkylated material. Secondary amine (19) is then converted to the title compound by reacting with a carboxylic acid or carboxylic acid equivalent to provide (Id).

SCHEME 4

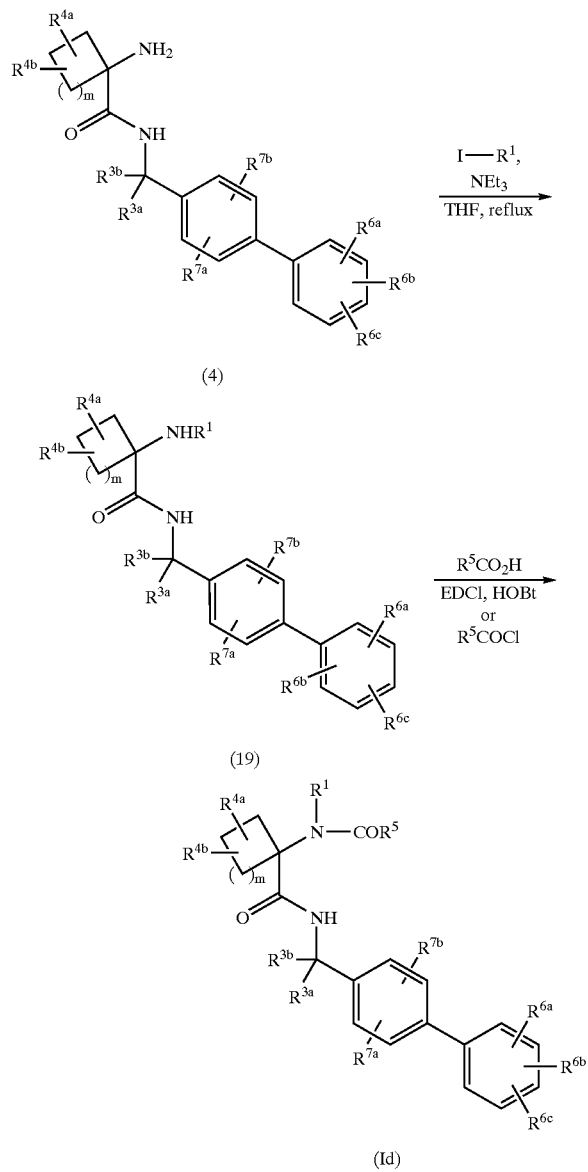

ment with sulfonyl chloride, and the sulfonate may be converted to the corresponding halide by treatment with a source of the halide. These and other functional transformations to provide compounds of formula I are described in typical organic chemistry textbooks such as March's Advanced Organic Chemistry: Reactions, Mechanisms, and Structure, $5^{th}$ Ed., John Wiley & Sons, 2000.

SCHEME 5

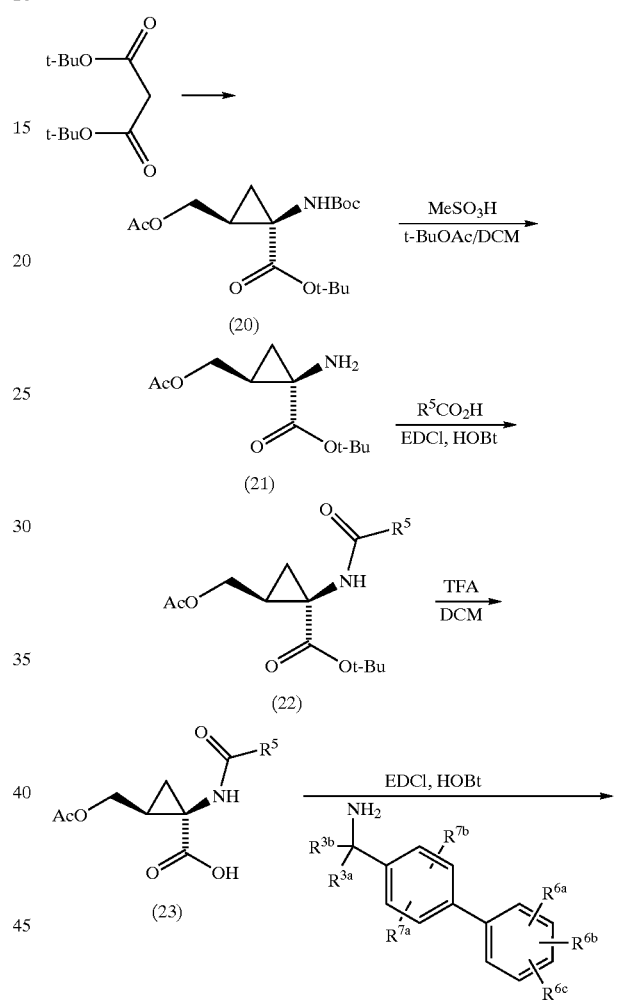

The preparation of compounds of formula I having a 1,2-cis- or 1,2-trans-cyclopropyl moiety is illustrated in Schemes 5 and 6. According to known procedures (K. Burgess et al., *J. Org. Chem.*, 57:5931–5936(1992)), di-tert-butyl malonate is elaborated to derivative (20). The N-Boc group is removed using methane sulfonic acid according to L. S. Lin et al. *Tetrahedron Lett.*, 41:7013–7016(2000) to give amine (21). This amine is allowed to react with a carboxylic acid or carboxylic acid equivalent under appropriate peptide coupling conditions to yield (22). The tert-butyl ester is then cleaved with an acid, like TFA, in an appropriate solvent, like DCM, to provide acid (23). Biarylmethanamine (1) is then coupled with the acid (23) using an appropriate set of peptide coupling reagents, like EDCI/HOBt, to produce the title compound (Ie). Further elaboration of (Ie) to additional compounds of formula I may be accomplished using procedures well known to those skilled in the art. For example, the acetyl group may be removed by hydrolysis to provide the corresponding alcohol; the alcohol may be converted to the corresponding sulfonate by treat-

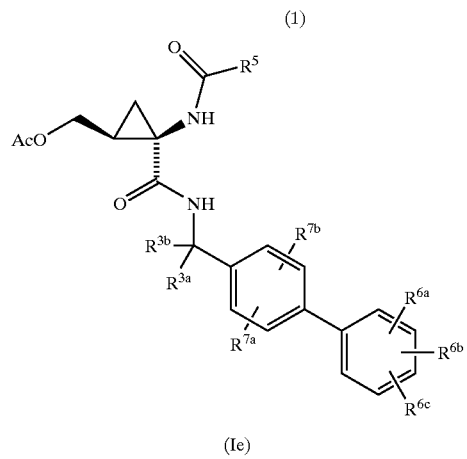

In Scheme 6, according to known procedures (K. Burgess et al., *J. Org. Chem.*, 57:5931–5936(1992)), di-tert-butyl malonate is elaborated to derivative (24). The N-Boc group is removed using an acid, like TFA, in an appropriate solvent, like DCM. This amine is allowed to react with a carboxylic acid or carboxylic acid equivalent under appropriate peptide coupling conditions, like EDCI/HOBt/NEt$_3$ to yield (25). Biarylmethanamine (1), is then allowed to open the lactone (25) in an appropriate aprotic solvent, like DMF, at a temperature between 20 and 100° C., to produce the title compound (If). Further elaboration of (If) to additional title compounds may be accomplished using procedures well known to those skilled in the art as previously discussed.

SCHEME 6

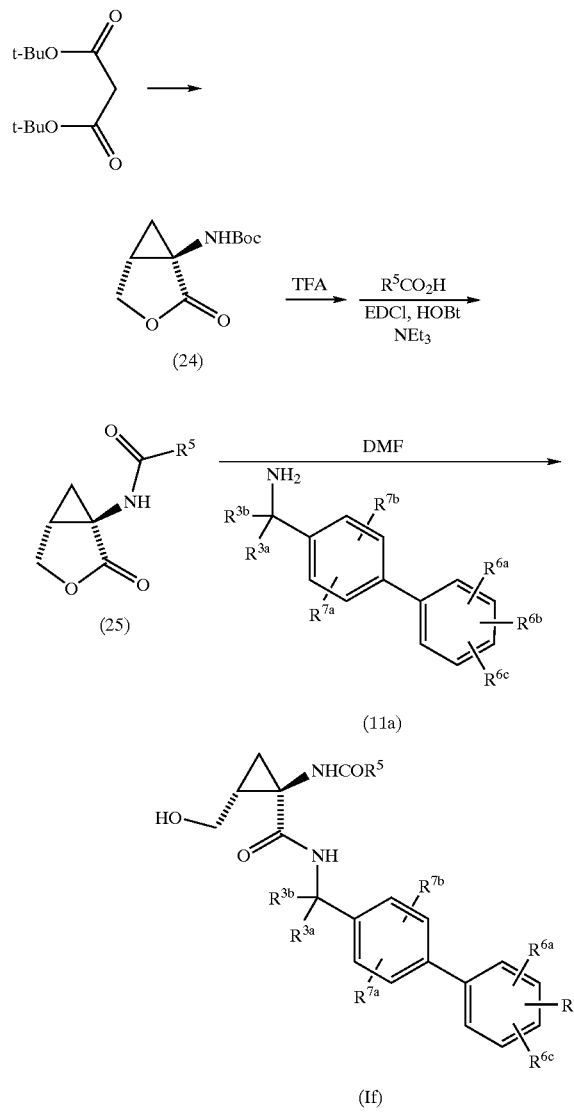

The following examples are provided to illustrate the invention without limiting the invention to the particulars of these examples. Compounds were named using: ACD/Name version 4.53 (Advanced Chemistry Development Inc.© 1994–2000). Address: 90 Adelaide Street West, Toronto, Ontario, M5H 3V9, Canada.

EXAMPLE 1

Methyl 3-fluoro-4'-{(1R)-1-[({1-[(3,3,3-trifluoropropanoyl)amino]cyclopropyl}carbonyyl)amino]ethyl}-1,1'-biphenyl-2-carboxylate

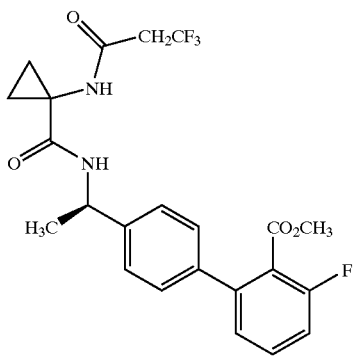

Commercially available (1R)-1-(4-bromophenyl)ethanamine was Boc protected, using standard procedures known to those skilled in the art, to produce tert-butyl (1R)-1-(4-bromophenyl)ethylcarbamate.

To a solution of tert-butyl (1R)-1-(4-bromophenyl)ethylcarbamate (7.6 g, 25.3 mmol) in DMSO (20 mL) was added bis(pinacolato)diboron (7.07 g, 27.9 mmol), dichloro[1,1'-bis(diphenylphosphino)ferrocene]palladium (II) dichloromethane adduct (2.06 g, 2.53 mmol), and potassium acetate (7.45 g, 76.0 mmol) at room temperature under N$_2$. The resulting mixture was heated at 80° C. for 1 hour. The reaction was quenched by addition of EtOAc and filtered through celite. The organic extract was washed with water three times, saturated NaCl, dried over MgSO$_4$, filtered and concentrated under vacuum. The residue was purified on silica gel eluted with 0–20% ethyl acetate in hexane to provide tert-butyl (1R)-1-[4-(4,4,5,5-tetramethyl-1,3,2-dioxaborolan-2-yl)phenyl]ethylcarbamate as a clear light yellow oil with a mass ion (ES+) of 333.

To a stirred solution of tert-butyl (1R)-1-[4-(4,4,5,5-tetramethyl-1,3,2-dioxaborolan-2-yl)phenyl]ethylcarbamate (1.0 g, 2.9 mmol) and methyl 2-fluoro-6-iodobenzoate (1.2 g, 4.32 mmol) in 25 mL of a 5:1 THF:water mixture was added potassium carbonate (1.2 g, 8.64 mmol), tri-o-tolylphosphine (350 mg, 1.15 mmol) and lastly palladium acetate (65 mg, 0.29 mmol). The reaction vessel was then sealed and placed into a 90° C. oil bath for overnight stirring and heating. After about 18 hours the reaction mixture was cooled to ambient temperature and then diluted with EtOAc. The organics were washed with brine (×4), dried over sodium sulfate, filtered, and concentrated under reduced pressure to give an oil. This oil was subject to silica gel chromatography eluting with 10–60% EtOAc in hexanes to provide methyl 4'-{(1R)-1-[(tert-butoxycarbonyl)amino]ethyl}-3-fluoro-1,1'-biphenyl-2-carboxylate (205 mg), found to be pure by LC/MS and proton NMR.

Methyl 4'-{(1R)-1-[(tert-butoxycarbonyl)amino]ethyl}-3-fluoro-1,1'-biphenyl-2-carboxylate (205 mg, 0.60 mmol) dissolved in MeOH (15 mL) was cooled to 0° C. This homogenous solution was saturated with anhydrous hydrogen chloride and allowed to sit for 20 minutes. Dry nitrogen was then bubbled through the solution for about 30 minutes. Solvent was then removed under reduced pressure to yield an oily residue. The oil was then dissolved in DCM and the solvent removed. This process was repeated until a solid amine hydrochloride was obtained.

The above amine hydrochloride (85 mg, 0.27 mmol) along with 1-[(tert-butoxycarbonyl)amino]cyclopropanecarboxylic acid (55 mg, 0.27 mmol), HOBt.H$_2$O (8.4 mg, 0.05 mmol) and triethylamine (33 mg, 0.33 mmol) were dissolved in 4.5 mL of THF. To this room-temperature solution was added EDCI (74 mg, 0.38 mmol). After overnight stirring (ca. 16.5 h) the reaction mixture was diluted with water and EtOAc. The organic layer was washed successively with 1N HCl, 5% sodium bicarbonate, half-brine (×3) and then brine. The organic layer was dried over sodium sulfate, filtered and evaporated under reduced pressure to obtain a residue which was subjected to silica gel chromatography eluting with 1–6% MeOH in DCM. Collection of product containing fractions and removal of solvent yielded 108 mg (86%) of methyl 4'-{(1R)-1-[({1-[(tert-butoxycarbonyl)amino]cyclopropyl}carbonyl)amino]ethyl}-3-fluoro-1,1'-biphenyl-2-carboxylate.

Methyl 4'-{(1R)-1-[({1-[(tert-butoxycarbonyl)amino]cyclopropyl}carbonyl)amino]ethyl}-3-fluoro-1,1'-biphenyl-2-carboxylate (108 mg, 0.24 mmol) dissolved in MeOH (5.0 mL) was cooled to 0° C. This homogenous solution was saturated with anhydrous hydrogen chloride and allowed to sit for 30 minutes. Dry nitrogen was then bubbled through the solution for about 50 min. Solvent was then removed under reduced pressure to yield an oily residue. The oil was then dissolved in DCM and the solvent removed. This process being repeated until a solid amine hydrochloride was obtained.

The above amine hydrochloride (46 mg, 0.12 mmol) along with trifluoropropionic acid (15 mg, 0.12 mmol), HOBt.H$_2$O (3.6 mg, 0.02 mmol) and triethylamine (14 mg, 0.14 mmol) were dissolved in 1.6 mL of THF plus 1.6 mL of DMF. To this room-temperature solution was added EDCI (31 mg, 0.16 mmol). After overnight stirring (ca. 18 h) the reaction mixture was diluted with water and EtOAc. The organic layer was washed successively with 1N HCl, 5% sodium bicarbonate, half-brine (×3) and then brine. The organic layer was dried over sodium sulfate, filtered and evaporated under reduced pressure to obtain a residue which was subjected to silica gel chromatography eluting with 1–12% MeOH in DCM. Collection of product containing fractions and removal of solvent yielded 36 mg (67%) of the title compound as a foaming solid. Purity was determined by LCMS (ES MS, M+H$^+$ found: 467) and proton NMR (400 MHz, CD$_3$OD): δ 7.555, 7.540, 7.535, 7.520, 7.515, 7.500, 7.393, 7.373, 7.319, 7.302, 7.298, 7.240, 7.222, 7.221, 7.211, 7.188, 7.167, 7.165, 5.116, 5.099, 5.081, 5.064, 3.659, 3.268, 3.241, 3.214, 3.187, 1.508, 1.490, 1.483, 1.477, 1.474, 1.470, 1.465, 1.454, 1.444, 1.056, 1.049, 1.036, 1.031, 1.023, 1.007, 0.999, 0.995, 0.982, 0.974).

EXAMPLE 2

3-Fluoro-N-methoxy-4'-{(1R)-1-[({1-[(3,3,3-trifluoropropanoyl)amino]cyclopropyl}carbonyl)amino]ethyl}-1,1'-biphenyl-2-carboxamide

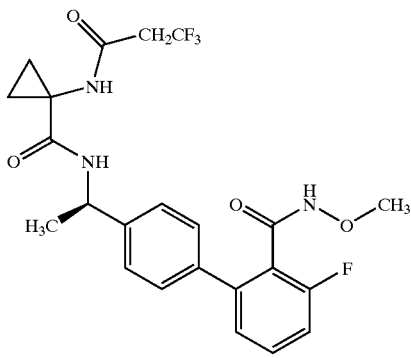

A solution of methyl 4'-{(1R)-1-[({1-[(tert-butoxycarbonyl)amino]cyclopropyl}carbonyl)amino]ethyl}-3-fluoro-1,1'-biphenyl-2-carboxylate (466 mg, 1.0 mmol) in DCM (15 mL) and TFA (15 mL) was stirred under N$_2$ for 20 minutes at ambient temperature, then the organic solvent was removed under vacuum. The residue was dissolved in MeOH (20 mL), 4N NaOH (10 mL) and water (10 mL). This mixture was heated at reflux for 4 hours and then neutralized with 6N HCl. Purification was achieved by preparative HPLC on a delta-pack C$_{18}$ column, 300 Å, pore size 15 μM with 0.05% HCl acid-aqueous acetonitrile solvent systems using various linear gradients. Fractions containing product of 99% purity as measured by HPLC were combined and lyophilized to give 4'-((1R)-1-{[(1-aminocyclopropyl)carbonyl]amino}ethyl)-3-fluoro-1,1'-biphenyl-2-carboxylic acid as a white solid.

To a solution of trifluoropropionic acid (128 mg, 1.0 mmol) in DCM (1 mL), 1-ethyl-(3-dimethylaminopropyl)carbodiimide hydrochloride (229 mg, 1.2 mmol) and 1-hydroxy-7-azabenzotriazole (136 mg, 1.0 mmol) were added. The resulting solution was stirred at room temperature for 20 minutes, then 4'-((1R)-1-{[(1-aminocyclopropyl)carbonyl]amino}ethyl)-3-fluoro-1,1'-biphenyl-2-carboxylic acid (171 mg, 0.5 mmol) in 1 mL DCM was added, followed by N,N-diisopropylethylamine until pH=10 was achieved. The reaction mixture was stirred at ambient temperature under N$_2$ for 2 hours, concentrated under vacuum and then partitioned between water and ethyl acetate. The organic extract was washed with brine, dried over anhydrous magnesium sulfate, filtered and concentrated under vacuum. The residue was subjected to column chromatography on silica gel eluted with 40% MeOH in CHCl$_3$. Collection and concentration of appropriate fractions provided 3-fluoro-4'-{(1R)-1-[({1-[(3,3,3-trifluoropropanoyl)amino]cyclopropyl}carbonyl)amino]ethyl}-1,1'-biphenyl-2-carboxylic acid as a white powder.

To a solution of the above acid (226 mg, 0.50 mmol) in DCM (1 mL), 1-ethyl-(3-dimethylaminopropyl)carbodiimide hydrochloride (134 mg, 0.70 mmol), 1-hydroxy-7-azabenzotriazole (68 mg, 0.50 mmol) and methoxyamine hydrochloride (167 mg, 1.0 mmol) were added, followed by N,N-diisopropylethylamine until pH=10 was achieved. The resulting solution was stirred at room temperature for 2 hours, and then partitioned between ethyl acetate and water. The organic extract was washed with brine, dried over anhydrous magnesium sulfate, filtered and concentrated under vacuum. Purification was achieved by preparative HPLC on a delta-pack C$_{18}$ column with 0.05% HCl acid-aqueous acetonitrile solvent systems using various linear gradients. Fractions containing product of 99% purity as measured by HPLC were combined and lyophilized to give the title compound as a white solid. Purity was determined by LCMS (ES MS, M+H$^+$ found:482) and proton NMR (400 MHz, DMSO-d$_6$) δ 1.40 (d, J=7.1 Hz, 3H), 0.60–0.80 (m, 2H), 1.27 (m, 2H), 3.23 (m, J=11.2 Hz, 2H). 3.44 (s, 3H), 5.02 (q, J=8 Hz, 1H), 7.25–7.39 (m, 6H), 7.52 (m, 1H), 7.93 (d, J=8.2 Hz, 1H), 8.89 (s, 1H).

EXAMPLE 3

Methyl 3-fluoro-4'-{1-methyl-1-[({1-[(trifluoroacetyl)amino]cyclopropyl}carbonyl)amino]ethyl}-1,1'-biphenyl-2-carboxylate

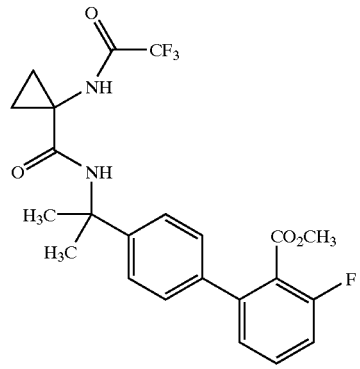

Methyl 2-(4-bromophenyl)-2-methylpropanoate (3.75 g, 14.6 mmol, prepared according to *J. Org. Chem.*, 59:2620–2622(1994)) in 150 mL of THF was allowed to react with potassium trimethylsilanolate (2.62 g, 20.4 mmol) at ambient temperature, for 60 hours, with continuous stirring. The reaction was then diluted with water and DCM. The pH of the aqueous phase was then adjusted to ca. 4, using 1M HCl. The aqueous layer was then extracted three times with additional DCM. The organic layers were pooled, dried over sodium sulfate, filtered and then concentrated to obtain 3.59 g of 2-(4-bromophenyl)-2-methylpropanoic acid, as a white solid, which gave LC/MS and proton NMR spectra consistent with theory.

To 82 mL of toluene was added the above acid (2.00 g, 8.23 mmol), triethylamine (1.20 mL, 8.64 mmol) and diphenylphosphoryl azide (1.86 mL, 8.64 mmol). After refluxing this mixture under nitrogen for 1 hour, benzyl alcohol (1.70 mL, 16.5 mmol) was added and the reaction mixture was allowed to reflux overnight. Solvent was removed under reduced pressure and the resulting oil was diluted with ethyl acetate. The ethyl acetate solution was washed twice with 5% sodium bicarbonate and once with brine. The organic layer was dried over sodium sulfate, filtered and evaporated under reduced pressure to obtain a residue which was subject to silica gel chromatography eluting with 0–2% MeOH in DCM. Collection of product containing fractions and removal of solvent yielded 2.26 grams of benzyl N-[1-(4-bromophenyl)-1-methylethyl]carbamate, which gave LC/MS and proton NMR spectra consistent with theory.

The above bromide (1.00 g, 2.87 mmol) was added to 25 mL of DMF, followed by bis(pinacolato)boron (0.875 g, 3.45 mmol), potassium acetate (0.846 g, 8.62 mmol) and PdCl$_2$(dppf)$_2$.CH$_2$Cl$_2$ (0.063 g, 0.090 mmol). This mixture was heated to 80° C., under nitrogen, for 3 hours. After cooling to ambient temperature, methyl 2-fluoro-6-iodobenzoate (0.965 g, 3.45 mmol), PdCl$_2$(dppf)$_2$.CH$_2$Cl$_2$ (0.063 g, 0.090 mmol) and aqueous sodium carbonate (7.18 mL, 2M, 14.4 mmol) were added. This mixture was then heated to 80° C. overnight. After cooling to ambient temperature, most of the DMF was removed under reduced pressure and the biphasic mixture was diluted with ethyl acetate. The pH of the aqueous layer was made neutral with 1M HCl, prior to extraction with two additional volumes of ethyl acetate. The combined organic layers were dried over sodium sulfate, filtered and evaporated under reduced pressure to obtain a residue which was subject to silica gel chromatography eluting with 0–2% MeOH in DCM. Collection of product containing fractions and removal of solvent yielded 0.25 grams of methyl 4'-(1-{[(benzyloxy)carbonyl]amino}-1-methylethyl)-3-fluoro-1,1'-biphenyl-2-carboxylate, which gave LC/MS and proton NMR spectra consistent with theory.

Methyl 4'-(1-{[(benzyloxy)carbonyl]amino}-1-methylethyl)-3-fluoro-1,1'-biphenyl-2-carboxylate (0.25 g, 0.59 mmol) was dissolved in 6.0 mL of anhydrous ethanol. Pd/C (90 mg) was then added and the nitrogen atmosphere was exchanged for hydrogen. The reaction mixture was allowed to stir for 72 hours. After filtration though celite, the ethanol was removed under reduced pressure to yield 0.15 grams of methyl 4'-(1-amino-1-methylethyl)-3-fluoro-1,1'-biphenyl-2-carboxylate which was of sufficient purity to use directly in the next reaction.

The above-mentioned amine (80 mg, 0.28 mmol), was dissolved in anhydrous DCM (4 mL). To this stirred solution was added 1-[(tert-butoxycarbonyl)amino]cyclopropanecarboxylic acid (67 mg, 0.33 mmol), HOBt.H$_2$O (8 mg, 0.08 mmol) and lastly EDCI (69 g, 0.36 mmol). This mixture was allowed to stir overnight. Solvent was then removed under reduced pressure and the residue was subjected to silica gel chromatography eluting with a 1–3% MeOH in DCM gradient to provide methyl 4'-{1-[({1-[(tert-butoxycarbonyl)amino]cyclopropyl}carbonyl)amino]-1-methylethyl}-3-fluoro-1,1'-biphenyl-2-carboxylate (82 mg), giving LC/MS and proton NMR spectra consistent with theory.

The above material (82 mg, 0.17 mmol) dissolved in ethyl acetate (4 mL) was cooled to 0° C. This homogenous solution was saturated with anhydrous hydrogen chloride and allowed to sit for 30 minutes. Dry nitrogen was then bubbled through the solution for about 30 minutes. Solvent was then removed under reduced pressure to yield an oily residue, which was used directly in the next reaction.

To a 0° C., stirred solution of the above mentioned amine (32 mg, 0.09 mmol) in DCM (2.0 mL) was added triethylamine (20 μL, 0.13 mmol) and lastly trifluoroacetic anhydride (20 μL, 0.11 mmol). After 10 minutes the ice bath was remove and stirring was continued for a total of 30 minutes The reaction mixture was subject to silica gel chromatography eluting with 0.5–2% MeOH in DCM. Collection of product containing fractions and removal of solvent yielded 34 mg (84%) of the title compound as a foaming solid. Purity was determined by LCMS (ES MS, M+H$^+$ found: 467) and proton NMR (400 MHz, CD$_3$OD : δ 7.552, 7.537, 7.531, 7.517, 7.512, 7.497, 7.442, 7.425, 7.420, 7.302, 7.297, 7.280, 7.250, 7.231, 7.203, 7.181, 7.159, 3.644, 1.664, 1.444, 1.432, 1.424, 1.412, 1.080, 1.068, 1.060, 1.048).

EXAMPLE 4

N-{(1R)-1-[3,3'-difluoro-2'-(3-methyl-1,2,4-oxadiazol-5-yl)-1,1'-biphenyl-4-yl]ethyl}-1-[(trifluoroacetyl)amino]cyclopropanecarboxamide

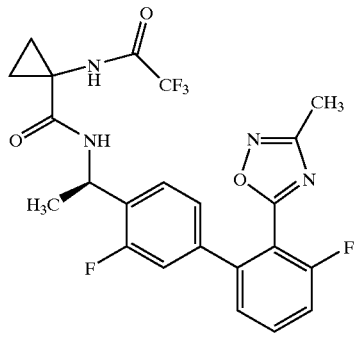

To a solution of 2-fluoro-6-iodobenzoic acid (15.00 g, 56.39 mmol) in 150 mL CH₂Cl₂ containing 0.1 mL DMF was added oxalyl chloride (9.30 g, 73.3 mmol) dropwise. The solution was stirred at room temperature for 75 minutes, then concentrated in vacuo. The residue was re-dissolved in 150 mL CH₂Cl₂, and the solution was saturated three times with ammonia gas. The solution was concentrated in vacuo and dried under vacuum overnight. The residue was dissolved in N,N-dimethylacetamide dimethyl acetal (24.7 mL, 0.169 mol) and heated to 120° C. for 5 hours. Additional N,N-dimethylacetamide dimethyl acetal (25 mL, 0.17 mol) was added over the course of the reaction to drive it to completion. The solution was cooled to room temperature, concentrated in vacuo, and dried under vacuum overnight. To a solution of the intermediate in 57 mL dioxane was added hydroxylamine hydrochloride (4.704 g, 67.69 mmol), 5N NaOH (13.5 mL, 67.7 mmol), and 70% acetic acid (57 mL). The mixture was stirred at 60° C. for 2 hours, then at 90° C. for 3 hours. The resulting solution was cooled to room temperature, diluted with ethyl acetate, and neutralized with aqueous sodium bicarbonate. The organic extract was washed with aqueous sodium bicarbonate and brine, dried over sodium sulfate, filtered and concentrated under vacuum. The residue was filtered through silica gel eluted with 10% ethyl acetate in hexanes to provide 5-(2-fluoro-6-iodophenyl)-3-methyl-1,2,4-oxadiazole as orange yellow crystals that gave proton NMR spectra consistent with theory and a mass ion (ES+) of 305.06 for M+H⁺.

To a solution of (S)-(−)-2-methyl-2-propanesulfinamide (20.20 g, 0.167 mol) in 350 mL CH₂Cl₂ were added 4-bromo-2-fluorobenzaldehyde (35.53 g, 0.1750 mol), pyridinium-p-toluenesulfonate (2.09 g, 8.33 mmol), and magnesium sulfate (200.6 g, 1.667 mol). The reaction mixture was stirred at room temperature for 48 hours. Additional magnesium sulfate (100.3 g, 0.833 mol) was added, and the reaction was stirred 24 hours. The mixture was filtered through celite, washing with CH₂Cl₂ and concentrated in vacuo. The resulting residue was subjected to column chromatography on silica gel eluted with 0–10% ethyl acetate in hexanes to afford N-[(1E)-(4-bromo-2-fluorophenyl)methylidene]-2-methylpropane-2-sulfinamide as a white solid that gave proton NMR spectra consistent with theory and a mass ion (ES+) of 308.09 for M+H⁺ (⁸¹Br).

To a solution of N-[(1E)-(4-bromo-2-fluorophenyl)methylidene]-2-methylpropane-2-sulfinamide (32.65 g, 0.1066 mol) in 550 mL CH₂Cl₂ at −48° C. was added methylmagnesium chloride (3.0 M solution is ether, 53.31 mL, 0.1599 mol) dropwise. The reaction was quenched with aqueous ammonium chloride and the aqueous layer was extracted with methylene chloride. The combined organics were dried over Na₂SO₄, filtered and concentrated under vacuum. The resulting residue was subjected to column chromatography on silica gel eluted with 10–50% ethyl acetate in hexanes to afford N-[(1R)-1-(4-bromo-2-fluorophenyl)ethyl]-2-methylpropane-2-sulfinamide as a white solid that gave proton NMR spectra consistent with theory and a mass ion (ES+) of 324.14 for M+H⁺ (⁸¹Br).

To a solution of N-[(1R)-1-(4-bromo-2-fluorophenyl)ethyl]-2-methylpropane-2-sulfinamide (26.29 g, 81.58 mmol) in 40 mL methanol was added HCl/dioxane (4M, 40.8 mL, 0.163 mol) solution. The reaction mixture was concentrated in vacuo, and ether was added. The white solid was collected, washing with cold ether, and dried under vacuum to yield (1R)-1-(4-bromo-2-fluorophenyl)ethanaminium chloride that gave proton NMR spectra consistent with theory.

To a solution of the above (1R)-1-(4-bromo-2-fluorophenyl)-ethanaminium chloride (14.24 g, 55.95 mmol) in 300 mL CH₂Cl₂ at 0° C. was added di-tert-butyl dicarbonate (17.98 g, 82.40 mmol) and triethylamine (8.256 g, 81.58 mmol). The solution was washed with water and brine, dried over Na₂SO₄, filtered and concentrated under vacuum to provide crude (1R)-1-(4-bromo-2-fluorophenyl)ethanaminium chloride as a white solid that gave proton NMR spectra consistent with theory.

A mixture of (1R)-1-(4-bromo-2-fluorophenyl)ethanaminium chloride (26.42 g, 83.03 mmol), bis(pinacolato)diboron (31.63 g, 0.1246 mol), potassium acetate (24.45 g, 0.2491 mol), and [1,1'-bis(diphenylphosphino)ferrocene]palladium(II) dichloride (0.265 g, 0.362 mmol) in 80 mL DMSO was heated to 90° C. under N₂ for 3 hours. The mixture was then cooled to room temperature and partitioned between ethyl acetate and water. The organic extract was washed with water and brine, dried over Na₂SO₄, filtered and concentrated under vacuum. The residue was subjected to silica gel chromatography eluted with 0–10% ethyl acetate in hexanes to provide tert-butyl (1R)-1-[2-fluoro-4-(4,4,5,5-tetramethyl-1,3,2-dioxaborolan-2-yl)phenyl]carbonate as a beige solid that gave proton NMR spectra consistent with theory.

A mixture of 5-(2-fluoro-6-iodophenyl)-3-methyl-1,2,4-oxadiazole (1.50 g, 4.93 mmol), tert-butyl (1R)-1-[2-fluoro-4-(4,4,5,5-tetramethyl-1,3,2-dioxaborolan-2-yl)phenyl]ethylcarbonate (1.80 g, 4.93 mmol), potassium carbonate (1.70 g, 12.3 mmol), tri-o-tolylphosphine (0.060 g, 0.20 mmol), and palladium acetate (0.011 g, 0.05 mmol) in 25 mL of THF and 4 mL of water was heated in a sealed flask at 100° C. overnight. The mixture was then cooled and concentrated in vacuo. The resulting residue was dissolved in ethyl acetate, washed with water and brine, dried over Na₂SO₄, filtered and concentrated under vacuum. The residue was subjected to silica gel chromatography eluted with 0–10% ethyl acetate and hexane to provide tert-butyl (1R)-1-[3,3'-difluoro-2'-(3-methyl-1,2,4-oxadiazol-5-yl)-1,1'-biphenyl-4-yl]ethylcarbamate as a yellow oil that gave proton NMR spectra consistent with theory. The product was dissolved in ethyl acetate and saturated with HCl gas. The solution was concentrated in vacuo and azeotroped 3 times with toluene to provide (1R)-1-[3,3'-difluoro-2'-(3-methyl-1,2,4-oxadiazol-5-yl)-1,1'-biphenyl-4-yl]ethanaminium chloride.

A solution of (1R)-1-[3,3'-difluoro-2'-(3-methyl-1,2,4-oxadiazol-5-yl)-1,1'-biphenyl-4-yl]ethanaminium chloride (0.500 g, 1.42 mmol), Boc-1-aminocyclo-propane-1-carboxylic acid (0.300 g, 1.49 mmol), 1-ethyl-(3-dimethylaminopropyl)carbodiimide hydrochloride (0.545 g, 2.84 mmol), 1-hydroxy-7-azabenzotriazole (0.010 g, 0.15 mmol), and triethylamine (0.863 g, 8.53 mmol) in 10 mL $CH_2Cl_2$ was stirred at room temperature overnight. The solution was washed with aqueous sodium bicarbonate and brine, dried over $Na_2SO_4$, filtered and concentrated. The residue was subjected to silica gel chromatography eluted with 10–40% ethyl acetate in hexanes to provide tert-butyl 1-[({(1R)-1-[3,3'-difluoro-2'-(3-methyl-1,2,4-oxadiazol-5-yl)-1,1'-biphenyl-4-yl]ethyl}amino)carbonyl] cyclopropylcarbamate as a white solid that gave proton NMR spectra consistent with theory. The product was dissolved in ethyl acetate and saturated with HCl gas. The solution was concentrated in vacuo and azeotroped 3 times with toluene to provide 1-[({(1R)-1-[3,3'-difluoro-2'-(3-methyl-1,2,4-oxadiazol-5-yl)-1,1'-biphenyl-4-yl]ethyl}amino)carbonyl]-cyclopropanaminium chloride that gave a mass ion (ES+) of 399.21 for M+H$^+$.

To a solution of the above compound (0.290 g, 0.667 mmol) in 5 mL $CH_2Cl_2$ at 0° C. was added triethylamine (0.135 g, 1.33 mmol) and trifluoroacetic anhydride (0.14 g, 0.67 mmol). The solution was diluted with addition $CH_2Cl_2$ and washed with aqueous sodium bicarbonate and brine, dried over $Na_2SO_4$, filtered and concentrated. The residue was subjected to silica gel chromatography eluted with 10–40% ethyl acetate in hexanes to provide the title compound that gave proton NMR spectra consistent with theory and a mass ion (ES+) of 495.22 for M+H$^+$: $^1$H NMR (300 MHz, MeOH-d$_4$) δ 9.71 (s, 1H), 8.29 (d, J=8.3 Hz, 1H), 7.77–7.70 (m, 1H), 7.41–7.30 (m, 3H), 6.95 (s, 1H), 6.93–6.91 (m, 1H), 5.32–5.22 (m, 1H), 2.36 (s, 3H), 1.51–1.45 (m, 5H), 1.15–1.01 (m, 2H).

EXAMPLE 5

Methyl 3-chloro-3'-fluoro-4'-{(1R)-1-[({1-[(trifluoroacetyl)amino]cyclopropyl}carbonyl)amino]ethyl}-1,1'-biphenyl-2-carboxylate

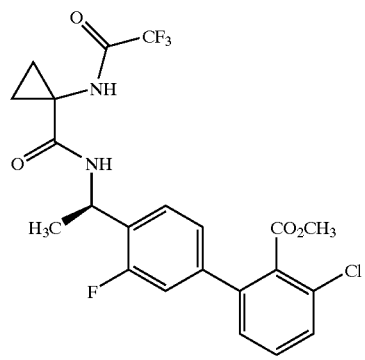

To a solution of n-BuLi (2.5M in hexanes, 41.8 mL, 0.104 mol) in 400 mL THF at −78° C. was added 2,2,6,6-tetramethylpiperidine (14.76 g, 0.1045 mol) dropwise followed by 3-bromochlorobenzene (20.00 g, 0.1045 mol) dropwise. The mixture was stirred at −78° C. for 2 h, then quenched with dry ice and warmed to room temperature. The solution was concentrated in vacuo and the resulting residue was dissolved in water and washed with ether. To the aqueous fraction was added 1N HCl to pH=2, and the product was extracted with $CH_2C_{12}$. The combined organics were dried over $Na_2SO_4$, filtered and concentrated under vacuum to provide 2-bromo-6-chlorobenzoic acid that gave proton NMR spectra consistent with theory.

To a solution of 2-bromo-6-chlorobenzoic acid (17.7 g, 75.2 mmol) in methanol (200 mL) at 0° C. was added (trimethylsilyl)diazomethane (2M in hexanes, 100 mL, 0.200 mol). The solution was stirred at 0° C. for 1.5 hours, then warmed to room temperature and washed with aqueous sodium bicarbonate and brine, dried over $Na_2SO_4$, filtered and concentrated. The residue was subjected to silica gel chromatography eluted with 0–5% ethyl acetate in hexanes to provide methyl 2-bromo-6-chlorobenzoate as a pale yellow oil that gave proton NMR spectra consistent with theory.

A mixture of methyl 2-bromo-6-chlorobenzoate (2.25 g, 9.03 mmol), tert-butyl (1R)-1-[2-fluoro-4-(4,4,5,5-tetramethyl-1,3,2-dioxaborolan-2-yl)phenyl]ethylcarbonate (see Example 11, 3.00 g, 8.21 mmol), potassium carbonate (2.84 g, 20.5 mmol), tri-o-tolylphosphine (0.10 g, 0.33 mmol), and palladium acetate (0.018 g, 0.08 mmol) in 40 mL of THF and 4 mL of water was heated in a sealed flask at 100° C. for 4 h. The mixture was then cooled and concentrated in vacuo. The resulting residue was dissolved in ethyl acetate, washed with water and brine, dried over $Na_2SO_4$, filtered and concentrated under vacuum. The residue was subjected to silica gel chromatography eluted with 0–10% ethyl acetate and hexane to provide methyl 4'-{(1R)-1-[(tert-butoxycarbonyl)amino]ethyl}-3-chloro-3'-fluoro-1,1'-biphenyl-2-carboxylate that gave proton NMR spectra consistent with theory. The product was dissolved in ethyl acetate and saturated with HCl gas. The solution was concentrated in vacuo and azeotroped 3× with toluene to provide (1R)-1-[3'-chloro-3-fluoro-2'-(methoxycarbonyl)-1,1'-biphenyl-4-yl]ethanaminium chloride.

A solution of the above compound (1.00 g, 2.91 mmol), boc-1-aminocyclopropane-1-carboxylic acid (0.614 g, 3.05 mmol), 1-ethyl-(3-dimethylaminopropyl)carbodiimide hydrochloride (1.11 g, 5.81 mmol), 1-hydroxy-7-azabenzotriazole (0.010 g, 0.15 mmol), and triethylamine (1.76 g, 17.4 mmol) in 20 mL $CH_2Cl_2$ was stirred at room temperature overnight. The solution was washed with aqueous sodium bicarbonate and brine, dried over $Na_2SO_4$, filtered and concentrated. The residue was subjected to silica gel chromatography eluted with 10–40% ethyl acetate in hexanes to provide methyl 4'-{(1R)-1-[({1-[(tert-butoxycarbonyl)amino]cyclopropyl}carbonyl)amino]ethyl}-3-chloro-3'-fluoro-1,1'-biphenyl-2-carboxylate as a white solid that gave proton NMR spectra consistent with theory. The product was dissolved in ethyl acetate and saturated with HCl gas. The solution was concentrated in vacuo and azeotroped three times with toluene to provide 1-[({(1R)-1-[3'-chloro-3-fluoro-2'-(methoxycarbonyl)-1,1'-biphenyl-4-yl]ethyl}amino)carbonyl]cyclopropanaminium chloride that gave a mass ion (ES+) of 391.21 for M+H$^+$.

To a solution of the above compound (0.300 g, 0.702 mmol) in 5 mL $CH_2Cl_2$ at 0° C. was added triethylamine (0.142 g, 1.40 mmol) and trifluoroacetic anhydride (0.147 g, 0.70 mmol). The solution was diluted with addition $CH_2Cl_2$ and washed with aqueous sodium bicarbonate and brine, dried over $Na_2SO_4$, filtered and concentrated. The residue was subjected to silica gel chromatography eluted with 10–40% ethyl acetate in hexanes to provide the title compound that gave proton NMR spectra consistent with theory and a mass ion (ES+) of 487.22 for M+H$^+$: $^1$H NMR (300 MHz, MeOH-d$_4$) δ 7.51–7.33 (m, 4H), 7.17–7.07 (m, 2H), 5.31 (q, J=7.1 Hz, 1H), 3.69 (s, 3H), 1.52–1.49 (m, 5H), 1.27–1.03 (m, 2H).

EXAMPLE 6

N-{(1R)-1-[3,3'-difluoro-2'-(2-methyl-2H-tetrazol-5-yl)-1,1'-biphenyl-4-yl]ethyl}-1-[(trifluoroacetyl)amino]cyclopropanecarboxamide

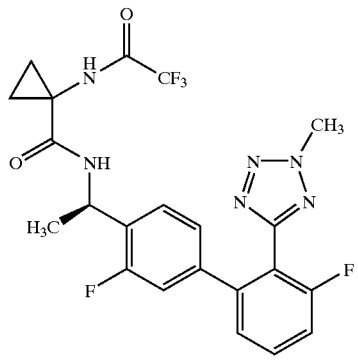

A solution of 2-fluoro-6-iodobenzonitrile (17.82 g, 72.15 mmol) and azidotrimethyltin (15.00 g, 72.88 mmol) in 150 mL toluene was heated to 125° C. for 72 hours. The solution was cooled to room temperature and partitioned between ethyl acetate and 0.5 N HCl. The organic extract was washed with water and brine, dried over $Na_2SO_4$, filtered and concentrated under vacuum to provide 5-(2-fluoro-6-iodophenyl)-1H-tetrazole that gave proton NMR spectra consistent with theory and a mass ion (ES+) of 291.01 for M+H$^+$.

A mixture of 5-(2-fluoro-6-iodophenyl)-1H-tetrazole (23.48 g, 80.97 mmol), potassium carbonate (16.79 g, 0.121 mol), and iodomethane (16.09 g, 0.113 mol) in 25 mL DMF was stirred at room temperature for 3 hours. The mixture was partitioned between ethyl acetate and water, and the organic extract was washed with water and brine, dried over $Na_2SO_4$, filtered and concentrated under vacuum. The residue was subjected to silica gel chromatography eluted with 0–10% ethyl acetate in hexanes to provide 5-(2-fluoro-6-iodophenyl)-2-methyl-2H-tetrazole that gave proton NMR spectra consistent with theory and a mass ion (ES+) of 305.06 for M+H$^+$.

To a solution of 2-fluoro-4-bromo-benzaldehyde (20.0 g, 98.5 mmol) in 500 mL of THF at 0° C. was added slowly a solution methyllithium (1.4 M in $Et_2O$, 70.3 mL). After one hour the reaction was carefully quenched with saturated aqueous ammonium chloride, extracted with diethyl ether, washed with saturated NaCl, dried over MgSO4, and concentrated. A solution of the crude alcohol in 200 mL of $CH_2Cl_2$ and TEA (14.0 mL, 100 mmol) at 0° C. was added methanesulfonyl chloride (7.42 mL, 95.9 mmol) over a period of five minutes. After and overnight reaction period, the reaction was extracted with $CH_2Cl_2$, washed with $NaHCO_3$, saturated NaCl, dried over $MgSO_4$, and concentrated. A solution of the crude mesylate in 50 mL of DMF was treated with sodium azide (12.5 g, 191 mmol) overnight. The reaction was extracted with EtOAc, washed with $NaHCO_3$, saturated NaCl, dried over $MgSO_4$, and concentrated. To a solution of the crude azide in 100 mL of THF was triethylphosphine (1 M in THF, 90.1 mL) over a period of 30 minutes. After one hour, 100 mL of 1 N HCl was added and the mixture was heated overnight. The mixture was cooled and washed with $Et_2O$. The aqueous layer was made basic by the addition of potassium carbonate, extracted with $Et_2O$, dried over $MgSO_4$, and concentrated. A solution of the crude amine (9.0 g, 41.2 mmol) in 50 mL of $CH_2Cl_2$ was treated with Boc anhydride (9.00 g, 41.2 mmol). After one hour the mixture was concentrated. A solution of the crude carbamate in 40 mL of DMSO was added potassium acetate (12.1 g, 123.1 mmol), bis(pinacolato)diboron (11.5 g, 45.4 mmol), and dichloro[1,1'-bis(diphenylphosphino)ferrocene] palladium (II) dichloromethane adduct (1.4 g, 1.8 mmol). The resulting mixture was heated at 80° C. for 16 hours. After cooling to room temperature, the mixture was partitioned between water and EtOAc. The organic extract was washed with brine, dried over $MgSO_4$, filtered and concentrated under vacuum. The residue was subjected to silica gel chromatography eluted with 20% ethyl acetate in hexanes to provide tert-butyl 1-[2-fluoro-4-(4,4,5,5-tetramethyl-1,3,2-dioxaborolan-2-yl)phenyl]ethylcarbamate as a tacky solid that gave a proton NMR consistent with theory.

A mixture of 5-(2-fluoro-6-iodophenyl)-2-methyl-2H-tetrazole (1.49 g, 4.89 mmol), tert-butyl 1-[2-fluoro-4-(4,4,5,5-tetramethyl-1,3,2-dioxaborolan-2-yl)phenyl]ethylcabamate (1.70 g, 4.65 mmol), potassium carbonate (1.61 g, 11.6 mmol), tri-o-tolylphosphine (0.057 g, 0.19 mmol), and palladium acetate (0.010 g, 0.05 mmol) in 20 mL of THF and 4 mL of water was heated in a sealed flask at 100° C. overnight. The mixture was then cooled and concentrated in vacuo. The resulting residue was dissolved in ethyl acetate, washed with water and brine, dried over $Na_2SO_4$, filtered and concentrated under vacuum. The residue was subjected to silica gel chromatography eluted with 0–20% ethyl acetate and hexane to provide tert-butyl 1-[3,3'-difluoro-2'-(2-methyl-2H-tetrazol-5-yl)-1,1'-biphenyl-4-yl]ethylcarbamate as a yellow oil that gave proton NMR spectra consistent with theory. The product was dissolved in ethyl acetate and saturated with HCl gas. The solution was concentrated in vacuo and azeotroped 3× with toluene to provide 1-[3,3'-difluoro-2'-(2-methyl-2H-tetrazol-5-yl)-1,1'-biphenyl-4-yl]ethanaminium chloride.

A solution of 1-[3,3'-difluoro-2'-(2-methyl-2H-tetrazol-5-yl)-1,1'-biphenyl-4-yl]ethanaminium chloride (0.670 g, 1.89 mmol), Boc-1-aminocyclopropane-1-carboxylic acid (0.419 g, 2.08 mmol), 1-ethyl-(3-dimethylaminopropyl) carbodiimide carboxylic acid (0.726 g, 3.79 mmol), 1-hydroxy-7-azabenzotriazole (0.010 g, 0.15 mmol), and triethylamine (1.15 g, 11.4 mmol) in 10 mL $CH_2Cl_2$ was stirred at room temperature for 48 hours. The solution was washed with aqueous sodium bicarbonate and brine, dried over $Na_2SO_4$, filtered and concentrated. The residue was subjected to silica gel chromatography eluted with 10–50% ethyl acetate in hexanes to provide tert-butyl 1-[({1-[3,3'-difluoro-2'-(2-methyl-2H-tetrazol-5-yl)-1,1'-biphenyl-4-yl]ethyl}amino)carbonyl]cyclopropylcarbamate that gave proton NMR spectra consistent with theory and a mass ion (ES+) of 499.7 for M+H$^+$. The enantiomers were resolved at this point on a Chiralcel OD column 10% isopropanol/hexane (containing 0.1% TFA). The R enantiomer eluted first and was used for the remainder of the synthesis.

The above product was dissolved in ethyl acetate and saturated with HCl gas. The solution was concentrated in vacuo and azeotroped 3× with toluene to provide (1R) 1-[({1-[3,3'-difluoro-2'-(2-methyl-2H-tetrazol-5-yl)-1,1'-biphenyl-4-yl]ethyl}amino)carbonyl]cyclopropanaminium chloride that gave a mass ion (ES+) of 399.6 for M+H$^+$.

To a solution of the above compound (0.105 g, 0.241 mmol) in 2 mL $CH_2Cl_2$ at 0° C. was added triethylamine (0.049 g, 0.48 mmol) and trifluoroacetic anhydride (0.051 g, 0.24 mmol). The solution was diluted with additional CH₂Cl₂ and washed with aqueous sodium bicarbonate and brine, dried over Na₂SO₄, filtered and concentrated. The residue was subjected to silica gel chromatography eluted with 10–40% ethyl acetate in hexanes to provide the title compound that gave proton NMR spectra consistent with theory and a mass ion (ES+) of 495.32 for M+H⁺: ¹H NMR (300 MHz, MeOH-d₄) δ 7.68–7.61 (m, 1H), 7.34–7.21 (m, 3H), 6.89–6.83 (m, 2H), 5.23 (d, J=7.1 Hz, 1H), 4.86 (s, 3H), 1.49 (d, J=3.7 Hz, 2H), 1.44 (d, J=7.1 Hz, 3H), 1.18–1.01 (m, 2H).

The following compounds in Table 1 were prepared by methods analogous to those described in Example 1.

TABLE 1

| Example | R⁵ | R⁶ᵇ | R⁷ᵃ | * | ES MS, M + H + |
|---|---|---|---|---|---|
| 7 | cyanomethyl | F | H | R | 424 |
| 8 | cyanomethyl | Cl | H | R | 440 |
| 9 | 2,2,2-trifluoroethyl | Cl | H | R | 482 |
| 10 | 2,2,2-trifluoroethyl | F | F | (±) | 485 |
| 11 | isoxazol-5-yl | F | F | (±) | 470 |
| 12 | cyanomethyl | F | F | (±) | 442 |
| 13 | pyrimidin-5-yl | F | H | R | 463 |
| 14 | 2,2,2-trifluoroethyl | F | F | S | 485 |
| 15 | 2,2,2-trifluoroethyl | F | F | R | 485 |
| 16 | pyrimidin-5-yl | F | F | (±) | 481 |
| 17 | isoxazol-5-yl | F | F | R | 470 |
| 18 | trifluoromethyl | F | F | R | 471 |
| 19 | pyrimidin-5-yl | F | F | R | 481 |
| 20 | isoxazol-5-yl | F | F | S | 470 |
| 21 | trifluoromethyl | F | F | S | 471 |
| 22 | pyrimidin-5-yl | F | F | S | 481 |
| 23 | methyl | F | F | R | 417 |
| 24 | 5-bromopyridin-3-yl | F | F | R | 558 |
| 25 | 5-bromo-1-oxido-pyridin-3-yl | F | F | R | 574 |
| 26 | trifluoromethyl | H | F | R | 453 |
| 27 | pyrimidin-5-yl | H | F | R | 463 |
| 28 | chlorodifluoromethyl | F | F | R | 487 |
| 29 | 5-(trifluoromethyl)-pyridin-3-yl | F | F | R | 548 |
| 30 | chlorodifluoromethyl | Cl | F | R | 503 |
| 31 | difluoromethyl | F | F | R | 453 |
| 32 | pentafluoroethyl | F | F | R | 521 |
| 33 | difluoromethyl | Cl | F | R | 469 |

*stereoconfiguration at designated chiral center (+) = racemic mixture

The following compounds in Table 2 were prepared by methods analogous to those described in Example 1.

TABLE 2

| Example | R⁵ | R⁶ᵇ | R⁷ᵃ | * | ES MS, M + H + |
|---|---|---|---|---|---|
| 34 | methyl | F | H | R | 423 |
| 35 | cyanomethyl | F | H | R | 448 |
| 36 | 2,2,2-trifluoroethyl | F | H | R | 491 |
| 37 | isoxazol-5-yl | F | H | R | 476 |
| 38 | 2,2,2-trifluoroethyl | F | F | S | 509 |
| 39 | 2,2,2-trifluoroethyl | F | F | R | 509 |
| 40 | cyanomethyl | F | F | (±) | 466 |
| 41 | 2,2,2-trifluoroethyl | F | F | (±) | 509 |
| 42 | pyrimidin-5-yl | F | F | (±) | 505 |
| 43 | chloro(difluoro)methyl | F | F | R | 511 |
| 44 | pyrimidin-5-yl | F | F | R | 505 |
| 45 | difluromethyl | F | F | R | 477 |

*stereoconfiguration at designated chiral center; (±) = racemic mixture

The following compounds in Table 3 were prepared by methods analogous to those described in Example 1.

TABLE 3

| Example | R⁵ | R⁷ᵃ | tetrazole | * | ES MS, M + H + |
|---|---|---|---|---|---|
| 46 | cyanomethyl | H | 2H | R | 448 |
| 47 | 2,2,2-trifluoroethyl | H | 2H | R | 491 |
| 48 | cyanomethyl | H | 1H | R | 448 |
| 49 | 2,2,2-trifluoroethyl | H | 1H | R | 491 |
| 50 | methyl | H | 1H | R | 423 |
| 51 | isoxazol-5-yl | F | 2H | (±) | 494 |
| 52 | 2,2,2-trifluoroethyl | F | 2H | (±) | 509 |
| 53 | pyrimidin-5-yl | F | 2H | (±) | 505 |
| 54 | trifluoromethyl | F | 2H | S | 495 |
| 55 | chloro(difluoro)methyl | F | 2H | R | 511 |
| 56 | difluoromethyl | F | 2H | R | 477 |

*stereoconfiguration at designated chiral center; (±) = racemic mixture

The following compounds in Table 4 were prepared by methods analogous to those described in Example 1.

TABLE 4

| Example | R⁵ | R⁶ᵃ | R⁶ᵇ | ES MS, M + H + |
|---|---|---|---|---|
| 57 | 2,2,2-trifluoroethyl | cyano | F | 434 |
| 58 | 2,2,2-trifluoroethyl | difluoromethoxy | H | 457 |
| 59 | 2,2,2-trifluoroethyl | trifluoromethoxy | H | 475 |
| 60 | 2,2,2-trifluoroethyl | trifluoromethyl | F | 478 |
| 61 | 2,2,2-trifluoroethyl | Cl | Cl | 459 |
| 62 | isoxazol-5-yl | trifluoromethyl | F | 462 |
| 63 | cyanomethyl | trifluoromethyl | F | 434 |
| 64 | isoxazol-5-yl | Cl | Cl | 444 |
| 65 | cyanomethyl | Cl | Cl | 416 |
| 66 | cyanomethyl | F | CO₂Me | 424 |
| 67 | cyclopropyl | cyano | F | 392 |
| 68 | 2,2,2-trifluoroethyl | (dimethylamino)carbonyl | F | 480 |
| 69 | pyrimidin-5-yl | (methoxycarbonyl)amino | F | 478 |
| 70 | pyrimidin-5-yl | [(methylamino)carbonyl]amino | F | 477 |
| 71 | trifluoromethyl | (methylamino)carbonyl | F | 452 |
| 72 | trifluoromethyl | (methylamino)carbonyl | Cl | 468 |

The following compounds in Table 5 were prepared by methods analogous to those described in Example 2.

TABLE 5

| Example | R⁵ | R⁶ᵃ | ES MS, M + H + |
|---|---|---|---|
| 73 | 2,2,2-trifluoroethyl | (methylamino)carbonyl | 466 |
| 74 | isoxazol-5-yl | (methoxyamino)carbonyl | 467 |
| 75 | 2,2,2-trifluoroethyl | (cyclopropylamino)carbonyl | 492 |
| 76 | 2,2,2-trifluoroethyl | (cyclobutylamino)carbonyl | 506 |

The following compounds in Table 6 were prepared by methods analogous to those described in Example 1.

TABLE 6

| Example | R⁵ | R⁶ᵇ | R⁶ᶜ | R⁷ᵃ | ES MS, M + H + |
|---|---|---|---|---|---|
| 77 | 2,2,2-trifluoroethyl | F | H | H | 491 |
| 78 | isoxazol-5-yl | F | H | H | 476 |
| 79 | pyrimidin-5-yl | H | H | F | 487 |
| 80 | trifluoromethyl | H | H | F | 477 |
| 81 | pyrimidin-5-yl | H | Cl | F | 521 |
| 82 | trifluoromethyl | H | Cl | F | 511 |
| 83 | pyrimidin-5-yl | H | methyl | F | 501 |
| 84 | trifluoromethyl | H | methyl | F | 491 |
| 85 | pyrimidin-5-yl | H | F | F | 505 |
| 86 | trifluoromethyl | H | F | F | 495 |

The following compounds in Table 7 were prepared by methods analogous to those described in Example 1.

TABLE 7

| Ex. | R⁵ | R⁶ᵃ | R⁶ᵇ | R⁶ᶜ | R⁷ᵃ | ES MS, M + H + |
|---|---|---|---|---|---|---|
| 87 | pyrimidin-5-yl | methoxy | F | F | H | 453 |
| 88 | trifluoromethyl | methoxy | F | F | H | 443 |
| 89 | pyrimidin-5-yl | 2-methyl-2H-tetrazol-5-yl | H | F | F | 505 |
| 90 | trifluoromethyl | 2-methyl-2H-tetrazol-5-yl | H | F | F | 495 |
| 91 | trifluoromethyl | CO₂Me | H | Cl | F | 487 |
| 92 | chlorodifluoromethyl | CO₂Me | H | Cl | F | 503 |
| 93 | trifluoromethyl | CO₂Me | H | methyl | F | 467 |
| 94 | chlorodifluoromethyl | CO₂Me | H | methyl | F | 483 |
| 95 | trifluoromethyl | 3-methyl-1,2,4-oxadiazol-5-yl | H | F | F | 495 |
| 96 | trifluoromethyl | 3-methyl-1,2,4-oxadiazol-5-yl | H | Cl | F | 511 |
| 97 | chlorodifluoromethyl | 3-methyl-1,2,4-oxadiazol-5-yl | H | Cl | F | 527 |
| 98 | trifluoromethyl | 3-methyl-1,2,4-oxadiazol-5-yl | H | methyl | F | 491 |
| 99 | chlorodifluoromethyl | 3-methyl-1,2,4-oxadiazol-5-yl | H | methyl | F | 507 |
| 100 | trifluoromethyl | CO₂Me | H | F | F | 471 |
| 101 | chlorodifluoromethyl | CO₂Me | H | F | F | 487 |
| 102 | pyrimidin-5-yl | 2-methyl-2H-tetrazol-5-yl | H | Cl | F | 521 |
| 103 | trifluoromethyl | 2-methyl-2H-tetrazol-5-yl | H | Cl | F | 511 |
| 104 | pyrimidin-5-yl | 2-methyl-2H-tetrazol-5-yl | H | methyl | F | 501 |
| 105 | trifluoromethyl | 2-methyl-2H-tetrazol-5-yl | H | methyl | F | 491 |
| 106 | trifluoromethyl | (methylamino)carbonyl | Cl | H | F | 486 |
| 107 | trifluoromethyl | (methoxycarbonyl)amino | Cl | H | F | 502 |
| 108 | trifluoromethyl | (isopropoxycarbonyl)-amino | Cl | H | F | 530 |
| 109 | pyrimidin-5-yl | (isopropoxy-carbonyl)amino | Cl | H | F | 540 |
| 110 | trifluoromethyl | (methoxycarbonyl)amino | F | H | F | 486 |
| 111 | trifluoromethyl | 2-methoxy-2-oxoethyl | F | H | F | 485 |
| 112 | trifluoromethyl | (methylamino)carbonyl | F | H | F | 470 |
| 113 | trifluoromethyl | methoxymethyl | Cl | H | F | 473 |
| 114 | trifluoromethyl | hydroxy | Cl | Cl | H | 479 |
| 115 | pyrimidin-5-yl | (methoxycarbonyl)amino | F | H | F | 496 |
| 116 | pyrimidin-5-yl | (methoxycarbonyl)amino | Cl | H | F | 512 |

The following compounds in Table 8 were prepared by methods analogous to those described in Example 1.

TABLE 8

| Example | $R^5$ | $R^{6b}$ | $R^{6c}$ | ES MS, M + H + |
|---|---|---|---|---|
| 117 | trifluoromethyl | H | methyl | 467 |
| 118 | chloro(difluoro)methyl | H | methyl | 483 |
| 119 | trifluoromethyl | Cl | H | 487 |
| 120 | trifluoromethyl | methyl | H | 467 |
| 121 | chloro(difluoro)methyl | methyl | H | 483 |

The following compounds in Table 9 were prepared by methods analogous to those described in Example 3, using the commercially available 1-[(tert-butoxycarbonyl)amino]cyclobutanecarboxylic acid instead of 1-[(tert-butoxycarbonyl)amino]cyclopropanecarboxylic acid.

TABLE 9

| Example | $R^{3a}, R^{3b}$ | $R^{6b}$ | $R^{7a}$ | ES MS, M + H + |
|---|---|---|---|---|
| 122 | Me, Me | F | H | 491 |

The following compounds in Table 10 were prepared by methods analogous to those described in Example 1, using the commercially available 1-[(tert-butoxycarbonyl)amino]cyclobutanecarboxylic acid instead of 1-[(tert-butoxycarbonyl)amino]cyclopropanecarboxylic acid.

TABLE 10

| Example | $R^5$ | $R^{6a}$ | $R^{6b}$ | $R^{7a}$ | ES MS, M + H+ |
|---|---|---|---|---|---|
| 123 | trifluoromethyl | 3-methyl-1,2,4-oxadiazol-5-yl | F | F | 509 |
| 124 | chlorodifluoromethyl | 3-methyl-1,2,4-oxadiazol-5-yl | F | F | 525 |
| 125 | pyrimidin-5-yl | 3-methyl-1,2,4-oxadiazol-5-yl | F | F | 519 |
| 126 | trifluoromethyl | $CO_2Me$ | F | F | 485 |
| 127 | chlorodifluoromethyl | $CO_2Me$ | F | F | 501 |
| 128 | pyrimidin-5-yl | $CO_2Me$ | F | F | 495 |
| 129 | pyrimidin-5-yl | $CO_2Me$ | F | H | 477 |
| 130 | pyrimidin-5-yl | 2-methyl-2H-tetrazol-5-yl | F | F | 519 |
| 131 | trifluoromethyl | $CO_2Me$ | Cl | F | 501 |
| 132 | chlorodifluoromethyl | $CO_2Me$ | Cl | F | 517 |
| 133 | difluoromethyl | $CO_2Me$ | Cl | F | 483 |

What is claimed is:

1. A compound of formula I or a pharmaceutically acceptable salt thereof:

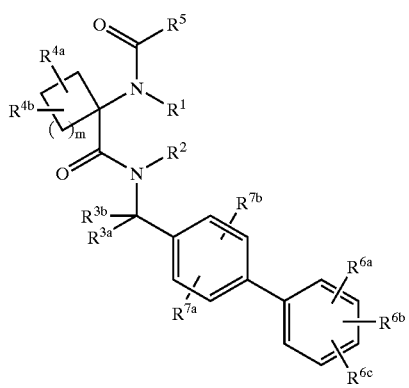

I wherein
$R^1$ and $R^2$ are independently selected from
  (1) hydrogen and
  (2) $C_{1-4}$ alkyl;
$R^{3a}$ is selected from
  (1) hydrogen and (2) $C_{1-4}$ alkyl optionally substituted with 1 to 5 halogen atoms;

$R^{3b}$ is $C_{1-4}$ alkyl optionally substituted with 1 to 5 halogen atoms;

$R^{4a}$ and $R^{4b}$ are independently selected form
(1) hydrogen,
(2) halogen, and
(3) $C_{1-4}$ alkyl optionally substituted with 1 to 4 groups selected from halogen, $OR^a$, $OC(O)R^a$, $S(O)_kR^d$, $OS(O)_2R^d$, and $NR^1R^2$, or $R^{4a}$ and $R^{4b}$ together with the carbon atom to which they are both attached form an exo-cyclic methylene optionally substituted with 1 to 2 groups selected from $C_{1-4}$ alkyl optionally substituted with 1–5 halogens and $C_{1-4}$ alkyloxy;

$R^5$ is selected from
(1) $C_{1-6}$ alkyl optionally substituted with 1 to 5 groups independently selected from halogen, nitro, cyano, $OR^a$, $SR^a$, $COR^a$, $SO_2R^d$, $CO_2R^a$, $OC(O)R^a$, $NR^bR^c$, $NR^bC(O)R^a$, $NR^bC(O)_2R^a$, $C(O)NR^bR^c$, $C_{3-8}$ cycloalkyl,
(2) $C_{3-8}$ cycloalkyl optionally substituted with 1 to 5 groups independently selected from halogen, nitro, cyano and phenyl,
(3) $C_{3-6}$ alkynyl,
(4) $C_{2-6}$ alkenyl optionally substituted with hydroxyethyl,
(5) $(CH_2)_k$-aryl optionally substituted with 1 to 3 groups independently selected from halogen, nitro, cyano, $OR^a$, $SR^a$, $C(O)_2R^a$, $C_{1-4}$ alkyl and $C_{1-3}$ haloalkyl, wherein aryl is selected from phenyl, 3,4-methylenedioxyphenyl and naphthyl;
(6) $(CH_2)_k$-heterocycle optionally substituted with 1 to 3 groups independently selected from halogen, nitro, cyano, $OR^a$, $SR^a$, $C_{1-4}$ alkyl and $C_{1-3}$ haloalkyl wherein said heterocycle is selected from (a) a 5-membered heteroaromatic ring having a ring heteroatom selected from N, O and S, and optionally having up to 3 additional ring nitrogen atoms wherein said ring is optionally benzo-fused; (b) a 6-membered heteroaromatic ring containing from 1 to 3 ring nitrogen atoms and N-oxides thereof, wherein said ring is optionally benzo-fused; and (c) a 5- or 6-membered non-aromatic heterocyclic ring selected from tetrahydrofuranyl, 5-oxotetrahydrofuranyl, 2-oxo-2H-pyranyl, 6-oxo-1,6-dihydropyridazinyl,
(7) $C(O)_2R^a$, and
(8) $C(O)NR^bR^c$;

$R^{6a}$ is selected from
(1) $C_{1-8}$ alkyl optionally substituted with 1–5 groups independently selected from halogen, nitro, cyano, $COR^a$, $CO_2R^a$, $C(O)NR^bR^c$, $OR^a$, $OC(O)R^a$, $SR^a$, $SO_2R^d$, $S(O)R^d$, $NR^bR^c$, $NR^bC(O)R^a$, $NR^bSO_2R^d$, $NR^bCO_2R^a$,
(2) $C_{3-8}$ cycloalkyl,
(3) $C_{2-8}$ alkenyl optionally substituted with $CO_2R^a$,
(4) halogen,
(5) cyano,
(6) nitro,
(7) $NR^bR^c$,
(8) $NR^bC(O)R^a$,
(9) $NR^bCO_2R^a$,
(10) $NR^bC(O)NR^bR^c$,
(11) $NR^bC(O)NR^bCO_2R^a$,
(12) $NR^bSO_2R^d$,
(13) $CO_2R^a$,
(14) $COR^a$,
(15) $C(O)NR^bR^c$,
(16) $C(O)NHOR^a$,
(17) $C(=NOR^a)R^a$,
(18) $C(=NOR^a)NR^bR^c$,
(19) $OR^a$,
(20) $OC(O)R^a$,
(21) $S(O)_kR^d$,
(22) $SO_2NR^bR^c$, and
(23) optionally substituted heterocycle where the heterocycle is a 5-membered heteroaromatic ring having a ring heteroatom selected from N, O and S, and optionally having up to 3 additional ring nitrogen atoms, 4,5-dihydro-oxazolyl and 4,5-dihydro-1,2,4-oxadiazolyl, and wherein said substituent is 1 to 3 groups independently selected from $C_{1-4}$ alicyl optionally substituted with 1 to 5 halogen atoms, $OR^a$ or $OC(O)R^a$, $R^{6b}$ and $R^{6c}$ are independently selected from
(1) hydrogen, and
(2) a group from $R^{6a}$; with the proviso that not more than one of $R^{6a}$, $R^{6b}$, and $R^{6c}$ is a heterocycle;

$R^{7a}$ and $R^{7b}$ are independently selected from
(1) hydrogen,
(2) halogen,
(3) cyano,
(4) nitro,
(5) $OR^a$,
(6) $CO_2R^a$,
(7) $C(O)NR^bR^c$,
(8) $C_{1-4}$ alkyl optionally substituted with 1 to 5 halogen atoms,
(9) $NR^bR^c$, and
(10) $S(O)_kR^d$;

$R^a$ is selected from
(1) hydrogen,
(2) $C_{1-4}$ alkyl optionally substituted with 1 to 5 halogen atoms,
(3) phenyl optionally substituted with 1 to 3 groups independently selected from halogen, cyano, nitro, OH, $C_{1-4}$ alkyloxy, $C_{3-6}$ cycloalkyl and $C_{1-4}$ alkyl optionally substituted with 1 to 5 halogen atoms,
(4) $C_{3-6}$ cycloalkyl, and
(5) pyridyl optionally substituted with 1 to 3 groups independently selected from halogen and $C_{1-4}$ alkyl;

$R^b$ and $R^c$ are independently selected from
(1) hydrogen,
(2) $C_{1-4}$ alkyl optionally substituted with 1 to 5 groups independently selected from halogen, amino, mono-$C_{1-4}$alkylamino, di-$C_{1-4}$alkylamino, and $SO_2R^d$,
(3) $(CH_2)_k$-phenyl optionally substituted with 1 to 3 groups selected from halogen, cyano, nitro, OH, $C_{1-4}$ alkyloxy, $C_{3-6}$ cycloalkyl and $C_{1-4}$ alkyl optionally substituted with 1 to 5 halogen atoms, and
(4) $C_{3-6}$ cycloalkyl, or $R^b$ and $R^c$ together with the nitrogen atom to which they are attached form a 4-, 5-, or 6-membered ring optionally containing an additional heteroatom selected from N, O, and S; or $R^b$ and $R^c$ together with the nitrogen atom to which they are attached form a cyclic imide;

$R^d$ is selected from
(1) $C_{1-4}$ alkyl optionally substituted with 1 to 5 halogen atoms,
(2) $C_{1-4}$ alkyloxy, and (3) phenyl optionally substituted with 1 to 3 groups selected from halogen, cyano, nitro, OH, $C_{1-4}$ alkyloxy, $C_{3-6}$ cycloalkyl and $C_{1-4}$ alkyl optionally substituted with 1 to 5 halogen atoms;

k is 0, 1 or 2; and m is 0 or 1.

2. A compound of claim 1 wherein $R^1$ and $R^2$ are each hydrogen.

3. A compound of claim 1 wherein $R^{3a}$ is hydrogen and $R^{3b}$ is $C_{1-4}$ alkyl.

4. A compound of claim 1 wherein one of $R^{4a}$ and $R^{4b}$ is hydrogen and the other is selected from hydrogen, halogen and $C_{1-4}$ alkyl optionally substituted with a group selected from halogen, $OR^a$, $OC(O)R^a$, $S(O)_kR^d$, $OS(O)_2R^d$ and $NR^1R^2$, or $R^{4a}$ and $R^{4b}$ together with the carbon atom to which they are both attached form an exo-cyclic methylene.

5. A compound of claim 1 wherein $R^{4a}$ and $R^{4b}$ are each hydrogen.

6. A compound of claim 1 wherein $R^5$ is $C_{1-6}$ alkyl optionally substituted with 1 to 5 groups independently selected from halogen, nitro, cyano, $OR^a$, $SR^a$, $COR^a$, $SO_2R^d$, $CO_2R^a$, $OC(O)R^a$, $NR^bR^c$, $NR^bC(O)R^a$, $C(O)NR^bR^c$, and $C_{3-8}$ cycloalkyl.

7. A compound of claim 1 wherein $R^5$ is selected from $C_{1-5}$ alkyl and $C_{1-3}$ alkyl substituted with 1 to 3 groups selected from halogen, cyano, hydroxy, $C_{1-4}$ alkoxy and $C_{1-4}$ alkoxycarbonyl.

8. A compound of claim 1 wherein $R^5$ is selected from $C_{1-3}$ alkyl substituted with 1 to 5 halogen atoms, or a group selected from cyano, hydroxy, $C_{1-4}$ alkoxy and $C_{1-4}$ alkoxycarbonyl.

9. A compound of claim 1 wherein $R^5$ is $C_{3-6}$ cycloalkyl optionally substituted with 1 to 3 groups independently selected from halogen, nitro, cyano and phenyl.

10. A compound of claim 1 wherein $R^5$ is $(CH_2)_k$-aryl optionally substituted with 1 to 3 groups independently selected from halogen, nitro, cyano, $OR^a$, $SR^a$, $C_{1-4}$ alkyl and $C_{1-3}$ haloalkyl, wherein aryl is selected from phenyl, 3,4-methylenedioxyphenyl and naphthyl.

11. A compound of claim 1 wherein $R^5$ is $(CH_2)_k$-heterocycle optionally substituted with 1 to 3 groups independently selected from halogen, nitro, cyano, $OR^a$, $SR^a$, $C_{1-4}$ alkyl and $C_{1-3}$ haloalkyl wherein said heterocycle is selected from (a) a 5-membered heteroaromatic ring having a ring heteroatom selected from N, O and S, and optionally having up to 3 additional ring nitrogen atoms wherein said ring is optionally benzo-fused; and (b) a 6-membered heteroaromatic ring containing from 1 to 3 ring nitrogen atoms wherein said ring is optionally benzo-fused.

12. A compound of claim 1 wherein $R^5$ is $(CH_2)_k$-heterocycle optionally substituted with 1 to 2 groups independently selected from halogen, nitro, cyano, $OR^a$, $SR^a$, $C_{1-4}$ alkyl and $C_{1-3}$ haloalkyl wherein said heterocycle is selected from isoxazolyl, thienyl, pyridinyl, benzothienyl, furyl, oxadiazolyl, 1-oxidopyndinyl, pyrazolyl, imidazolyl, 1,2,4-triazolyl, thiazolyl, 5-oxotetrahydrofuranyl, 2-oxo-2H-pyranyl, 6-oxo-1,6-dihydro-pyridazinyl, oxazolyl, pyridazinyl, pyrimidinyl and quinoxalinyl.

13. A compound of claim 1 wherein $R^5$ is selected from 5-isoxazolyl, 5-pyrimidinyl, 5-bromo-3-pyridyl and N-oxide thereof, and 5-trifluoromethyl-3-pyridyl.

14. A compound of claim 1 wherein $R^5$ is selected from isoxazolyl optionally substituted with $C_{1-4}$ alkyl, pyrimidinyl, pyridinyl optionally substituted with $C_{1-4}$ alkyl and N-oxides thereof.

15. A compound of claim 1 having the formula I(1):

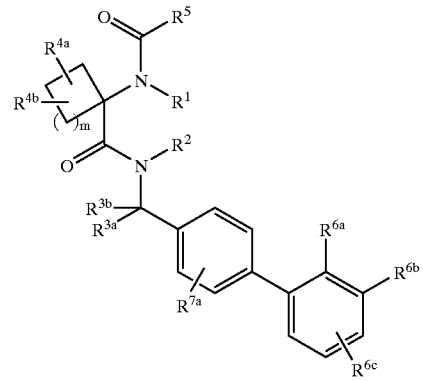

I(1)

wherein m, $R^1$, $R^2$, $R^{3a}$, $R^{3b}$, $R^{4a}$, $R^{4b}$, $R^5$, $R^{6a}$, $R^{6b}$, $R^{6c}$ and $R^{7a}$ are as defined in claim 1.

16. A compound of claim 15 wherein $R^{6a}$ is selected from (1) $CO_2R^a$, (2) $C(O)NHOR^a$, (3) cyano, (4) halogen, (5) $OR^a$, (6) $C_{1-8}$ alkyl optionally substituted with 1–5 halogen atoms, or a group selected from $CO_2R^a$, $C(O)NR^bR^c$ and $OR^a$, (7) $C(O)NR^bR^c$, (8) $NR^bC(O)NR^bR^c$, (9) $NR^bC(O)OR^a$, and (10) optionally substituted heterocycle where the heterocycle is selected from oxadiazolyl and tetrazolyl and wherein said substituent is 1 to 3 groups independently selected from $C_{1-4}$ alkyl optionally substituted with 1 to 5 halogen atoms, $OR^a$ or $OC(O)R^a$.

17. A compound of claim 15 wherein $R^{6a}$ is selected from $CO_2R^a$, $C(O)NHOR^a$, methyltetrazolyl, methyloxadiazolyl, $NR^bC(O)NR^bR^c$, and $NR^bC(O)OR^a$.

18. A compound of claim 15 wherein $R^{6b}$ is selected from hydrogen, halogen and $CO_2R^a$.

19. A compound of claim 15 wherein $R^{6b}$ is hydrogen or halogen.

20. A compound of claim 15 wherein $R^{6a}$ is selected from (1) $CO_2R^a$, (2) $C(O)NHOR^a$, (3) cyano, (4) halogen, (5) $OR^a$, (6) $C_{1-8}$ alkyl optionally substituted with 1–5 halogen atoms, or a group selected from $CO_2R^a$, $C(O)NR^bR^c$ and $OR^a$, (7) $C(O)NR^bR^c$, (8) $NR^bC(O)NR^bR^c$, (9) $NR^bC(O)OR^a$, and (10) optionally substituted heterocycle where the heterocycle is selected from oxadiazolyl and tetrazolyl and wherein said substituent is 1 to 3 groups independently selected from $C_{1-4}$ alkyl optionally substituted with 1 to 5 halogen atoms, $OR^a$ or $OC(O)R^a$; $R^{6b}$ is selected from hydrogen, fluorine and chlorine; and $R^{6c}$ is hydrogen.

21. A compound of claim 15 wherein $R^5$ is selected from $C_{1-4}$ alkyl optionally substituted with 1 to 5 halogen atoms or a cyano group, $C_{3-6}$ cycloalkyl, isoxazolyl, pyrimidinyl and pyridinyl (and N-oxide thereof) optionally substituted with halogen.

22. A compound of claim 1 having the formula I(2):

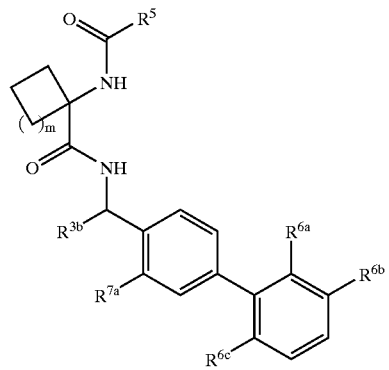

I(2)

wherein m, $R^{3b}$, $R^{4a}$, $R^{4b}$, $R^5$, $R^{6a}$, $R^{6b}$, $R^{6c}$ and $R^{7a}$ are as defined in claim 1.

23. A compound of claim 22 wherein $R^{3b}$ is methyl.
24. A compound of claim 22 wherein $R^{6b}$ is hydrogen or halogen.
25. A compound of claim 22 wherein $R^{6b}$ is hydrogen.
26. A compound of claim 22 wherein $R^{6b}$ is fluorine or chlorine.
27. A compound of claim 22 wherein $R^{6a}$ is selected from (1) $CO_2R^a$, (2) C(O)NHOR$^a$, (3) cyano, (4) halogen, (5) OR$^a$, (6) $C_{1-8}$ alkyl optionally substituted with 1–5 halogen atoms, or a group selected from $CO_2R^a$, C(O)NR$^b$R$^c$ and OR$^a$, (7) C(O)NR$^b$R$^c$, (8) NR$^b$C(O)NR$^b$R$^c$, (9) NR$^b$C(O)OR$^a$, and (10) optionally substituted heterocycle where the heterocycle is selected from oxadiazolyl and tetrazolyl and wherein said substituent is 1 to 3 groups independently selected from $C_{1-4}$ alkyl optionally substituted with 1 to 5 halogen atoms, OR$^a$ or OC(O)R$^a$.
28. A compound of claim 22 wherein $R^{6a}$ is selected from $CO_2R^a$, C(O)NHOR$^a$, methyltetrazolyl, methyloxadiazolyl, NR$^b$C(O)NR$^b$R$^c$, and NR$^b$C(O)OR$^a$.
29. A compound of claim 22 wherein $R^{6a}$ is selected from $CO_2R^a$, methyltetrazolyl and methyloxadiazolyl.

30. A compound of claim 22 wherein $R^{6c}$ is hydgrogen.
31. A compound of claim 22 wherein $R^{7a}$ is hydrogen or halogen.
32. A compound of claim 22 wherein $R^{7a}$ is hydrogen or fluorine.
33. A compound of claim 22 wherein $R^5$ is selected from $C_{1-4}$ alkyl optionally substituted with 1 to 5 halogen atoms or a cyano group, $C_{3-6}$ cycloalkyl, isoxazolyl, pyrimidinyl and pyridinyl (and N-oxide thereof) optionally substituted with halogen.

34. A compound of claim 1 having the formula I(3):

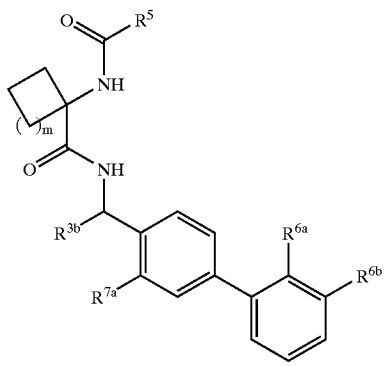

I(3)

wherein m is 0 or 1, $R^{6a}$ is 2-methyl-2H-tetrazol-5-yl, 3-methyl-1,2,4-oxadiazol-5-yl, $CO_2R^a$ or C(O)NHOR$^a$ wherein $R^a$ is $C_{1-4}$ alkyl; $R^{6b}$ is hydrogen, fluorine or chlorine; $R^{3b}$ is $C_{1-4}$ alkyl; $R^5$ is selected from $C_{1-4}$ alkyl optionally substituted with 1 to 5 halogen atoms or a cyano group, $C_{3-6}$ cycloalkyl, isoxazolyl, pyrimidinyl and pyridinyl (and N-oxide thereof) optionally substituted with halogen or trifluoromethyl, particularly trifluoromethyl, difluoromethyl, chlorodifluromethyl; and $R^{7a}$ is hydrogen or fluorine.

35. A compound selected from:

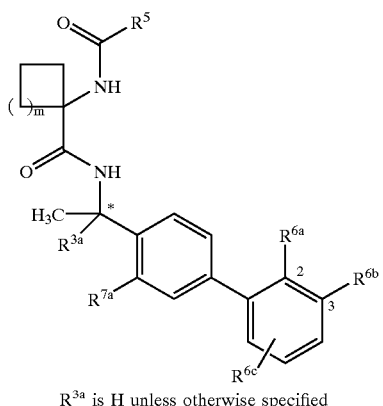

$R^{3a}$ is H unless otherwise specified

| m | $R^5$ | $R^{6a}$ | $R^{6b}$ | $R^{6c}$ | $R^{7a}$ | * |
|---|---|---|---|---|---|---|
| 0 | $CH_2CF_3$ | $CO_2CH_3$ | F | H | H | R |
| 0 | $CH_2CF_3$ | $CONHOCH_3$ | F | H | H | R |
| 0 | $CF_3$ | $CO_2CH_3$ | F | H | H | § |
| 0 | $CF_3$ | 3-$CH_3$-1,2,4-oxadiazol-5-yl | F | H | F | R |
| 0 | $CF_3$ | $CO_2CH_3$ | Cl | H | F | R |
| 0 | $CF_3$ | 2-$CH_3$-tetrazol-5-yl | F | H | F | R |
| 0 | $CH_2CN$ | $CO_2CH_3$ | F | H | H | R |

-continued

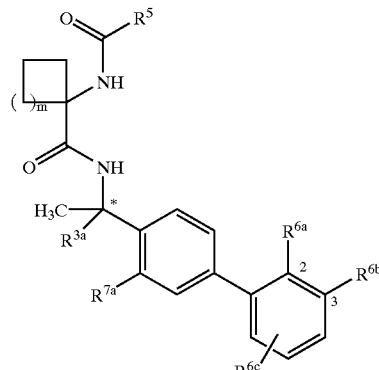

R³ᵃ is H unless otherwise specified

| m | R⁵ | R⁶ᵃ | R⁶ᵇ | R⁶ᶜ | R⁷ᵃ | * |
|---|---|---|---|---|---|---|
| 0 | CH₂CN | CO₂CH₃ | Cl | H | H | R |
| 0 | CH₂CF₃ | CO₂CH₃ | Cl | H | H | R |
| 0 | CH₂CF₃ | CO₂CH₃ | F | H | F | (±) |
| 0 | isoxazol-5-yl | CO₂CH₃ | F | H | F | (±) |
| 0 | CH₂CN | CO₂CH₃ | F | H | F | (±) |
| 0 | pyrimidin-5-yl | CO₂CH₃ | F | H | H | R |
| 0 | CH₂CF₃ | CO₂CH₃ | F | H | F | S |
| 0 | CH₂CF₃ | CO₂CH₃ | F | H | F | R |
| 0 | pyrimidin-5-yl | CO₂CH₃ | F | H | F | (±) |
| 0 | isoxazol-5-yl | CO₂CH₃ | F | H | F | R |
| 0 | CF₃ | CO₂CH₃ | F | H | F | R |
| 0 | pyrimidin-5-yl | CO₂CH₃ | F | H | F | R |
| 0 | isoxazol-5-yl | CO₂CH₃ | F | H | F | S |
| 0 | CF₃ | CO₂CH₃ | F | H | F | S |
| 0 | pyrimidin-5-yl | CO₂CH₃ | F | H | F | S |
| 0 | CH₃ | CO₂CH₃ | F | H | F | R |
| 0 | 5-Br-pyridin-3-yl | CO₂CH₃ | F | H | F | R |
| 0 | 5-Br-1-oxido-pyridin-3-yl | CO₂CH₃ | F | H | F | R |
| 0 | CF₃ | CO₂CH₃ | H | H | F | R |
| 0 | pyrimidin-5-yl | CO₂CH₃ | H | H | F | R |
| 0 | CClF₂ | CO₂CH₃ | F | H | F | R |
| 0 | 5-(CF₃)pyridin-3-yl | CO₂CH₃ | F | H | F | R |
| 0 | CClF₂ | CO₂CH₃ | Cl | H | F | R |
| 0 | CHF₂ | CO₂CH₃ | F | H | F | R |
| 0 | CF₂CF₃ | CO₂CH₃ | F | H | F | R |
| 0 | CHF₂ | CO₂CH₃ | Cl | H | F | R |
| 0 | CH₃ | 3-CH₃-1,2,4-oxadiazol-5-yl | F | H | H | R |
| 0 | CH₂CN | 3-CH₃-1,2,4-oxadiazol-5-yl | F | H | H | R |
| 0 | CH₂CF₃ | 3-CH₃-1,2,4-oxadiazol-5-yl | F | H | H | R |
| 0 | isoxazol-5-yl | 3-CH₃-1,2,4-oxadiazol-5-yl | F | H | H | R |
| 0 | CH₂CF₃ | 3-CH₃-1,2,4-oxadiazol-5-yl | F | H | F | S |
| 0 | CH₂CF₃ | 3-CH₃-1,2,4-oxadiazol-5-yl | F | H | F | R |
| 0 | CH₂CN | 3-CH₃-1,2,4-oxadiazol-5-yl | F | H | F | (±) |
| 0 | CH₂CF₃ | 3-CH₃-1,2,4-oxadiazol-5-yl | F | H | F | (±) |
| 0 | pyrimidin-5-yl | 3-CH₃-1,2,4-oxadiazol-5-yl | F | H | F | (±) |
| 0 | CClF₂ | 3-CH₃-1,2,4-oxadiazol-5-yl | F | H | F | R |
| 0 | pyrimidin-5-yl | 3-CH₃-1,2,4-oxadiazol-5-yl | F | H | F | R |
| 0 | CHF₂ | 3-CH₃-1,2,4-oxadiazol-5-yl | F | H | F | R |
| 0 | CH₂CN | 2-CH₃-tetrazol-5-yl | F | H | H | R |
| 0 | CH₂CF₃ | 2-CH₃-tetrazol-5-yl | F | H | H | R |
| 0 | CH₂CN | 1-CH₃-tetrazol-5-yl | F | H | H | R |
| 0 | CH₂CF₃ | 1-CH₃-tetrazol-5-yl | F | H | H | R |
| 0 | CH₃ | 1-CH₃-tetrazol-5-yl | F | H | H | R |
| 0 | isoxazol-5-yl | 2-CH₃-tetrazol-5-yl | F | H | F | (±) |
| 0 | CH₂CF₃ | 2-CH₃-tetrazol-5-yl | F | H | F | (±) |
| 0 | pyrimidin-5-yl | 2-CH₃-tetrazol-5-yl | F | H | F | (±) |
| 0 | CF₃ | 2-CH₃-tetrazol-5-yl | F | H | F | S |
| 0 | CClF₂ | 2-CH₃-tetrazol-5-yl | F | H | F | R |
| 0 | CHF₂ | 2-CH₃-tetrazol-5-yl | F | H | F | R |
| 0 | CH₂CF₃ | cyano | F | H | H | R |
| 0 | CH₂CF₃ | difluoromethoxy | H | H | H | R |
| 0 | CH₂CF₃ | trifluoromethoxy | H | H | H | R |
| 0 | CH₂CF₃ | trifluoromethyl | F | H | H | R |
| 0 | CH₂CF₃ | Cl | Cl | H | H | R |
| 0 | isoxazol-5-yl | trifluoromethyl | F | H | H | R |
| 0 | CH₂CN | trifluoromethyl | F | H | H | R |
| 0 | isoxazol-5-yl | Cl | Cl | H | H | R |

-continued

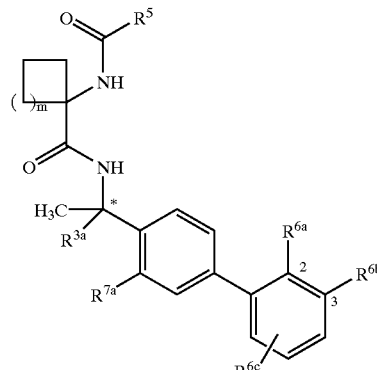

$R^{3a}$ is H unless otherwise specified

| m | $R^5$ | $R^{6a}$ | $R^{6b}$ | $R^{6c}$ | $R^{7a}$ | * |
|---|---|---|---|---|---|---|
| 0 | CH$_2$CN | Cl | Cl | H | H | R |
| 0 | CH$_2$CN | F | CO$_2$Me | H | H | R |
| 0 | cyclopropyl | cyano | F | H | H | R |
| 0 | CH$_2$CF$_3$ | CON(CH$_3$)$_2$ | F | H | H | R |
| 0 | pyrimidin-5-yl | NHCO$_2$CH$_3$ | F | H | H | R |
| 0 | pyrimidin-5-yl | NHCONHCH$_3$ | F | H | H | R |
| 0 | CF$_3$ | CONHCH$_3$ | F | H | H | R |
| 0 | CF$_3$ | CONHCH$_3$ | Cl | H | H | R |
| 0 | CH$_2$CF$_3$ | CONHCH$_3$ | F | H | H | R |
| 0 | isoxazol-5-yl | CONHOCH$_3$ | F | H | H | R |
| 0 | CH$_2$CF$_3$ | CONH-cyclopropyl | F | H | H | R |
| 0 | CH$_2$CF$_3$ | CONH-cyclobutyl | F | H | H | R |
| 0 | CH$_2$CF$_3$ | 5-CH$_3$-1,2,4-oxadiazol-3-yl | F | H | H | R |
| 0 | isoxazol-5-l | 5-CH$_3$-1,2,4-oxadiazol-3-yl | F | H | H | R |
| 0 | pyrimidin-5-yl | 5-CH$_3$-1,2,4-oxadiazol-3-yl | H | H | F | R |
| 0 | CF$_3$ | 5-CH$_3$-1,2,4-oxadiazol-3-yl | H | H | F | R |
| 0 | pynmidin-5-yl | 5-CH$_3$-1,2,4-oxadiazol-3-yl | H | 5-Cl | F | R |
| 0 | CF$_3$ | 5-CH$_3$-1,2,4-oxadiazol-3-yl | H | 5-Cl | F | R |
| 0 | pyrimidin-5-yl | 5-CH$_3$-1,2,4-oxadiazol-3-yl | H | 5-CH3 | F | R |
| 0 | CF$_3$ | 5-CH$_3$-1,2,4-oxadiazol-3-yl | H | 5-CH3 | F | R |
| 0 | pyrimidin-5-yl | 5-CH$_3$-1,2,4-oxadiazol-3-yl | H | 5-F | F | R |
| 0 | CF$_3$ | 5-CH$_3$-1,2,4-oxadiazol-3-yl | H | 5-F | F | R |
| 0 | pyrimidin-5-yl | methoxy | F | 5-F | H | R |
| 0 | CF$_3$ | methoxy | F | 5-F | H | R |
| 0 | pyrimidin-5-yl | 2-CH$_3$-2H-tetrazol-5-yl | H | 5-F | F | R |
| 0 | CF$_3$ | 2-CH$_3$-2H-tetrazol-5-yl | H | 5-F | F | R |
| 0 | CF$_3$ | CO$_2$CH$_3$ | H | 5-Cl | F | R |
| 0 | CClF$_2$ | CO$_2$CH$_3$ | H | 5-Cl | F | R |
| 0 | CF$_3$ | CO$_2$CH$_3$ | H | 5-CH$_3$ | F | R |
| 0 | CClF$_2$ | CO$_2$CH$_3$ | H | 5-CH$_3$ | F | R |
| 0 | CF$_3$ | 3-CH$_3$-1,2,4-oxadiazol-5-yl | H | 5-F | F | R |
| 0 | CF$_3$ | 3-CH$_3$-1,2,4-oxadiazol-5-yl | H | 5-Cl | F | R |
| 0 | CClF$_2$ | 3-CH$_3$-1,2,4-oxadiazol-5-yl | H | 5-Cl | F | R |
| 0 | CF$_3$ | 3-CH$_3$-1,2,4-oxadiazol-5-yl | H | 5-CH$_3$ | F | R |
| 0 | CClF$_2$ | 3-CH$_3$-1,2,4-oxadiazol-5-yl | H | 5-CH$_3$ | F | R |
| 0 | CF$_3$ | CO$_2$CH$_3$ | H | 5-F | F | R |
| 0 | CClF$_2$ | CO$_2$CH$_3$ | H | 5-F | F | R |
| 0 | pyrimidin-5-yl | 2-CH$_3$-2H-tetrazol-5-yl | H | 5-Cl | F | R |
| 0 | CF$_3$ | 2-CH$_3$-2H-tetrazol-5-yl | H | 5-Cl | F | R |
| 0 | pyrimidin-5-yl | 2-CH$_3$-2H-tetrazol-5-yl | H | 5-CH$_3$ | F | R |
| 0 | CF$_3$ | 2-CH$_3$-2H-tetrazol-5-yl | H | 5-CH3 | F | R |
| 0 | CF$_3$ | CONHCH$_3$ | Cl | H | F | R |
| 0 | CF$_3$ | NHCO$_2$CH$_3$ | Cl | H | F | R |
| 0 | CF$_3$ | NHCO$_2$CH(CH$_3$)$_2$ | Cl | H | F | R |
| 0 | pyrimidin-5-yl | NHCO$_2$CH(CH$_3$)$_2$ | Cl | H | F | R |
| 0 | CF$_3$ | NHCO$_2$CH$_3$ | F | H | F | R |
| 0 | CF$_3$ | 2-methoxy-2-oxoethyl | F | H | F | R |
| 0 | CF$_3$ | CONHCH$_3$ | F | H | F | R |
| 0 | CF$_3$ | CH$_2$OCH$_3$ | Cl | H | F | R |
| 0 | CF$_3$ | hydroxy | Cl | 5-Cl | H | R |
| 0 | pyrimidin-5-yl | NHCO$_2$CH$_3$ | F | H | F | R |
| 0 | pyrimidin-5-yl | NHCO$_2$CH$_3$ | Cl | H | F | R |
| 0 | CF$_3$ | CO$_2$CH$_3$ | H | 6-CH$_3$ | F | R |
| 0 | CClF$_2$ | CO$_2$CH$_3$ | H | 6-CH$_3$ | F | R |
| 0 | CF$_3$ | CO$_2$CH$_3$ | Cl | H | F | R |
| 0 | CF$_3$ | CO$_2$CH$_3$ | CH3 | H | F | R |
| 0 | CClF$_2$ | CO$_2$CH$_3$ | CH3 | H | F | R |

-continued

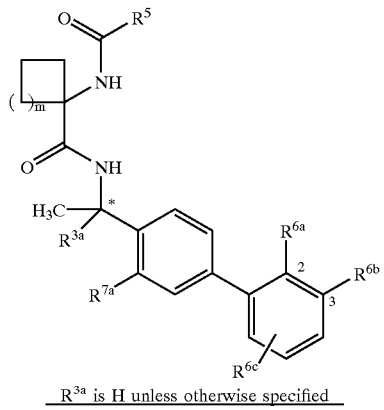

$R^{3a}$ is H unless otherwise specified

| m | $R^5$ | $R^{6a}$ | $R^{6b}$ | $R^{6c}$ | $R^{7a}$ | * |
|---|---|---|---|---|---|---|
| 1 | pyrimidin-5-yl | $CO_2CH_3$ | F | H | H | § |
| 1 | $CF_3$ | 3-$CH_3$-1,2,4-oxadiazol-5-yl | F | H | F | R |
| 1 | $CClF_2$ | 3-$CH_3$-1,2,4-oxadiazol-5-yl | F | H | F | R |
| 1 | pynmidin-5-yl | 3-$CH_3$-1,2,4-oxadiazol-5-yl | F | H | F | R |
| 1 | $CF_3$ | $CO_2CH_3$ | F | H | F | R |
| 1 | $CClF_2$ | $CO_2CH_3$ | F | H | F | R |
| 1 | pyrimidin-5-yl | $CO_2CH_3$ | F | H | F | R |
| 1 | pyrimidin-5-yl | $CO_2CH_3$ | F | H | H | R |
| 1 | pyrimidin-5-yl | 2-$CH_3$-2H-tetrazol-5-yl | F | H | F | R |
| 1 | $CF_3$ | $CO_2CH_3$ | Cl | H | F | R |
| 1 | $CClF_2$ | $CO_2CH_3$ | Cl | H | F | R |
| 1 | $CHF_2$ | $CO_2CH_3$ | Cl | H | F | R |

*stereoconfiguration at the indicated carbon, § $R^{3a}$ is $CH_3$; or a pharmaceutically acceptable salt thereof.

36. The compound methyl 3-chloro-3'-fluoro-4'-{(1R)-1-[({1-[(trifluoroacetyl)amino]cyclopropyl}carbonyl)amino]ethyl}-1,1'-biphenyl-2-carboxylate.

37. A pharmaceutical composition comprising a therapeutically effective amount of a compound of claim 1 and pharmaceutically acceptable excipients.

38. A pharmaceutical composition comprising a therapeutically effective amount of a compound of claim 36 and pharmaceutically acceptable excipients.

39. A method of treatment of osteoarthritis, repetitive motion pain, dental pain, cancer pain, myofascial pain, muscular injury pain, fibromyalgia pain, perioperative pain comprising a step of administering, to a subject in need of such treatment, an effective amount of a compound according to claim 1 or a pharmaceutically acceptable salt thereof.

40. A method of treatment of diabetic vasculopathy, post capillary resistance, diabetic symptoms associated with insulitis, psoriasis, eczema, spasms of the gastrointestinal tract or uterus, Crohn's disease, ulcerative colitis, or pancreatitis comprising a step of administering, to a subject in need of such treatment, an effective amount of a compound according to claim 1 or a pharmaceutically acceptable salt thereof.

* * * * *